US012766011B2

(12) United States Patent
Churchill et al.

(10) Patent No.: US 12,766,011 B2
(45) Date of Patent: Oct. 20, 2026

(54) IMPLANT DELIVERY DEVICE

(71) Applicant: EMBODY, INC., Norfolk, VA (US)

(72) Inventors: R. Sean Churchill, Grand Rapids, MI (US); Robert J. Ball, West Olive, MI (US); Douglas Snell, Grand Rapids, MI (US); Isaac Running, Grand Rapids, MI (US); Christopher K Jones, Colorado Springs, CO (US); Brandon Bryant, Vienna, VA (US); Stacy Blair, Norfolk, VA (US); Robert S. Brown, Norfolk, VA (US); Matthew Havener, Norfolk, VA (US)

(73) Assignee: Embody, Inc., Norfolk, VA (US)

( * ) Notice: Subject to any disclaimer, the term of this patent is extended or adjusted under 35 U.S.C. 154(b) by 617 days.

(21) Appl. No.: 18/226,560

(22) Filed: Jul. 26, 2023

(65) Prior Publication Data

US 2024/0033105 A1 Feb. 1, 2024

Related U.S. Application Data

(60) Provisional application No. 63/394,271, filed on Aug. 1, 2022.

(51) Int. Cl.
*A61F 2/46* (2006.01)
*A61F 2/28* (2006.01)
*A61F 2/30* (2006.01)

(52) U.S. Cl.
CPC .................................. *A61F 2/4612* (2013.01)

(58) Field of Classification Search
CPC .......... A61F 2/0063; A61F 2/011; A61F 2/28; A61F 2/30907; A61F 2/4601; A61F 2/4612; A61F 2002/0072; A61F 2002/2835; A61F 2002/30148; A61F 2002/30487; A61F 2002/4495; A61F 2002/4627; A61F 2002/4628; A61F 2230/0019; A61B 17/3468; A61B 2017/00367
See application file for complete search history.

(56) References Cited

U.S. PATENT DOCUMENTS

| | | | |
|---|---|---|---|
| 10,258,459 B2 * | 4/2019 | Zenz-Olson .......... | A61F 2/0805 |
| 10,617,787 B2 | 4/2020 | Francis et al. | |
| 10,653,817 B2 | 5/2020 | Francis et al. | |

(Continued)

*Primary Examiner* — Tan-Uyen T Ho
*Assistant Examiner* — Lindsey R. Rivers
(74) *Attorney, Agent, or Firm* — SCHWEGMAN LUNDBERG & WOESSNER, P.A.

(57) ABSTRACT

An implant delivery device may include a handle disposed at a proximal end of the implant delivery device and configured to be grasped by a user. The device may further include an outer shaft extending from the handle to a distal end of the implant delivery device. In addition, the implant delivery device may include an implant holding portion proximate the distal end of the implant delivery device, the implant holding portion being configured to retain a sheet-like implant during implantation of the implant. Further, the implant holding portion may be configured to receive the implant between a fixed implant supporting flange member and configured to support the implant on one side, and a movable implant supporting flange member. The fixed implant supporting flange member may include a pair of substantially triangular shaped wings extending from a centerline axis of the outer shaft.

20 Claims, 40 Drawing Sheets

(56) References Cited

U.S. PATENT DOCUMENTS

| | | | | |
|---|---|---|---|---|
| 11,559,330 | B2 | 1/2023 | Jones et al. | |
| 2003/0083747 | A1* | 5/2003 | Winterbottom ....... | A61F 2/4455 623/17.11 |
| 2004/0267304 | A1* | 12/2004 | Zannis .................. | A61F 2/4618 606/206 |
| 2005/0234395 | A1* | 10/2005 | Mackool ................ | A61B 46/10 604/35 |

* cited by examiner

IMPLANT DELIVERY DEVICE

CLAIM OF PRIORITY

This application claims the benefit of U.S. Provisional Patent Application Ser. No. 63/394,271, filed on Aug. 1, 2022, the benefit of priority of which is claimed hereby, and which is incorporated by reference herein in its entirety.

BACKGROUND

The present embodiments relate generally to medical devices, and in particular to medical devices used to repair tissue.

Rotator cuff repair is a surgical procedure performed to repair torn (or partially torn) tendons in the shoulder. This procedure can be done with large incisions or with arthroscopic techniques. To repair a torn tendon (such as the supraspinatus tendon), a surgeon may use anchors and sutures to reattach the tendon to the humerus bone. The repaired area may then be covered with a graft to facilitate healing. Inserting a graft through a small incision and laying it down in a desired position can be difficult with arthroscopic surgery.

There is a need in the art for a system and method that addresses the shortcomings discussed above.

SUMMARY

In one aspect, the present disclosure is directed to an implant delivery device including a handle disposed at a proximal end of the implant delivery device and configured to be grasped by a user. The device may further include an outer shaft extending from the handle to a distal end of the implant delivery device. In addition, the implant delivery device may include an implant holding portion proximate the distal end of the implant delivery device, the implant holding portion being configured to retain a sheet-like implant during implantation of the implant. Further, the implant holding portion may be configured to receive the implant between a fixed implant supporting flange member and configured to support the implant on one side, and a movable implant supporting flange member. The fixed implant supporting flange member may include a pair of substantially triangular shaped wings extending from a centerline axis of the outer shaft.

In another aspect, the present disclosure is directed to an implant delivery device. The device may include an implant holding portion proximate a distal end of the implant delivery device, the implant holding portion being configured to retain a sheet-like implant during implantation of the implant; and a fixed implant supporting flange member, wherein the fixed implant supporting flange member includes a pair of substantially triangular shaped wings extending from a centerline axis of the outer shaft.

In another aspect, the present disclosure is directed to a method of delivering a sheet-like implant to a surgical site. Providing the implant delivery device as described in either of the preceding paragraphs with a sheet-like implant secured by the implant holding portion of the implant delivery device such that the implant is held with respect to the outer shaft and between the fixed implant supporting flange member and the movable implant supporting flange member. The method may further include inserting the implant holding portion of the implant delivery device to a surgical site.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

For clarity, the description makes reference to distal and proximal directions (or portions). As used herein, the term "distal" shall refer to a direction or portion oriented or located away from a user who is holding the implant delivery device (i.e., away from a surgeon using the device and toward a patient into which the device is being inserted). The term "proximal" shall refer to a direction or portion oriented or located toward a user who is holding the implant delivery device (i.e., toward a surgeon using the device and away from a patient into which the device is being inserted).

In addition, as used herein, the term "fixedly attached" shall refer to two components joined in a manner such that the components may not be readily separated (for example, without destroying one or both components). The term "removably attached" shall refer to components that are attached to one another in a readily separable manner (for example, with fasteners, such as bolts, screws, etc.).

Figure 1:
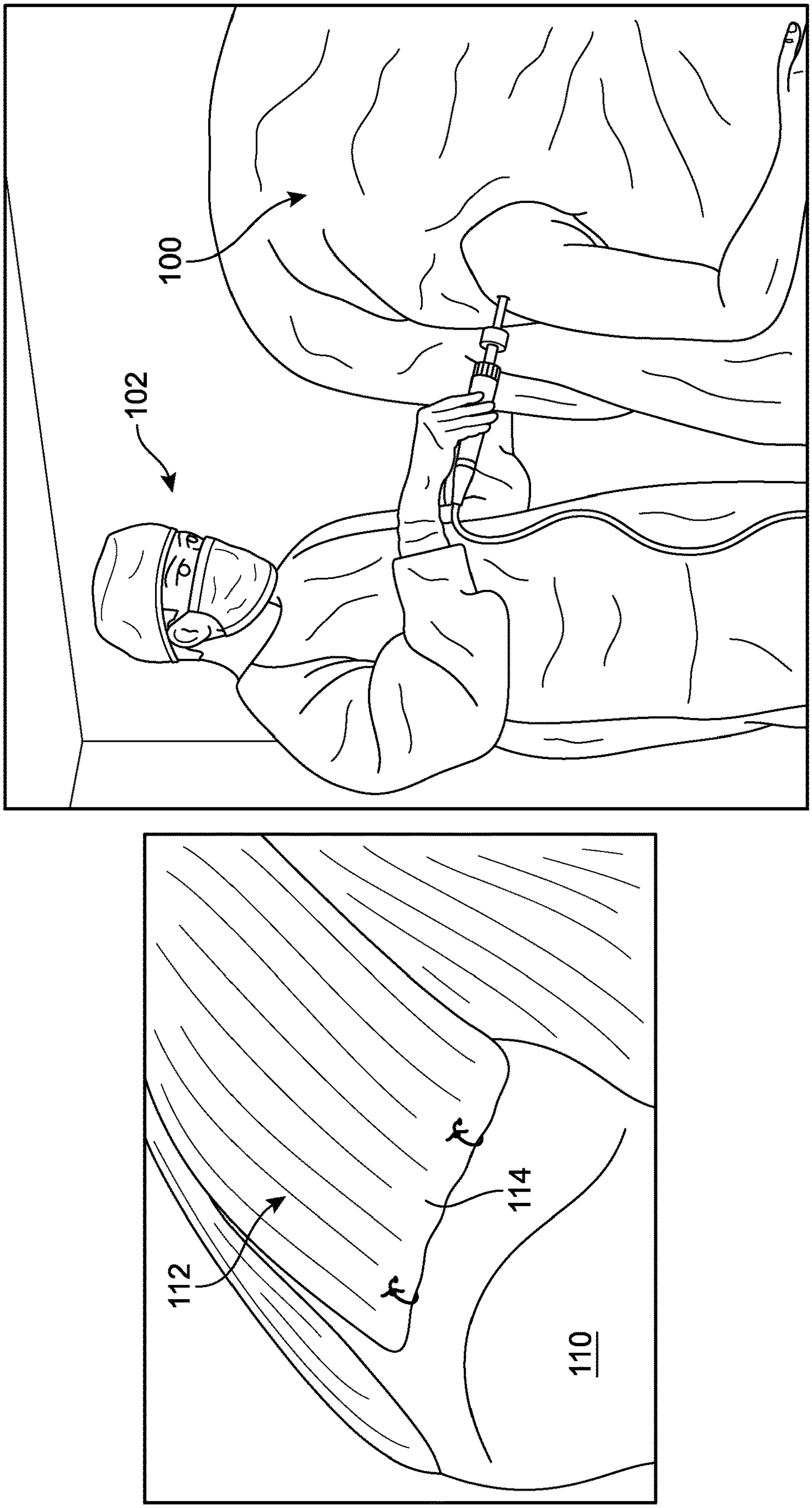
FIG. 1 is a schematic view of a step in a procedure for repairing a rotator cuff tendon according to an embodiment.

FIG. 1 is a schematic view illustrating a surgical procedure to repair a tendon in a patient's shoulder. Specifically, a patient 100 is undergoing arthroscopic surgery that is performed by surgeon 102. Also shown in FIG. 1 is an enlarged view of a portion of humerus 110 and rotator cuff tendons 112. In the present example, surgeon 102 has recently applied anchors and sutures to secure supraspinatus tendon 114 to humerus 110.

Figure 2:
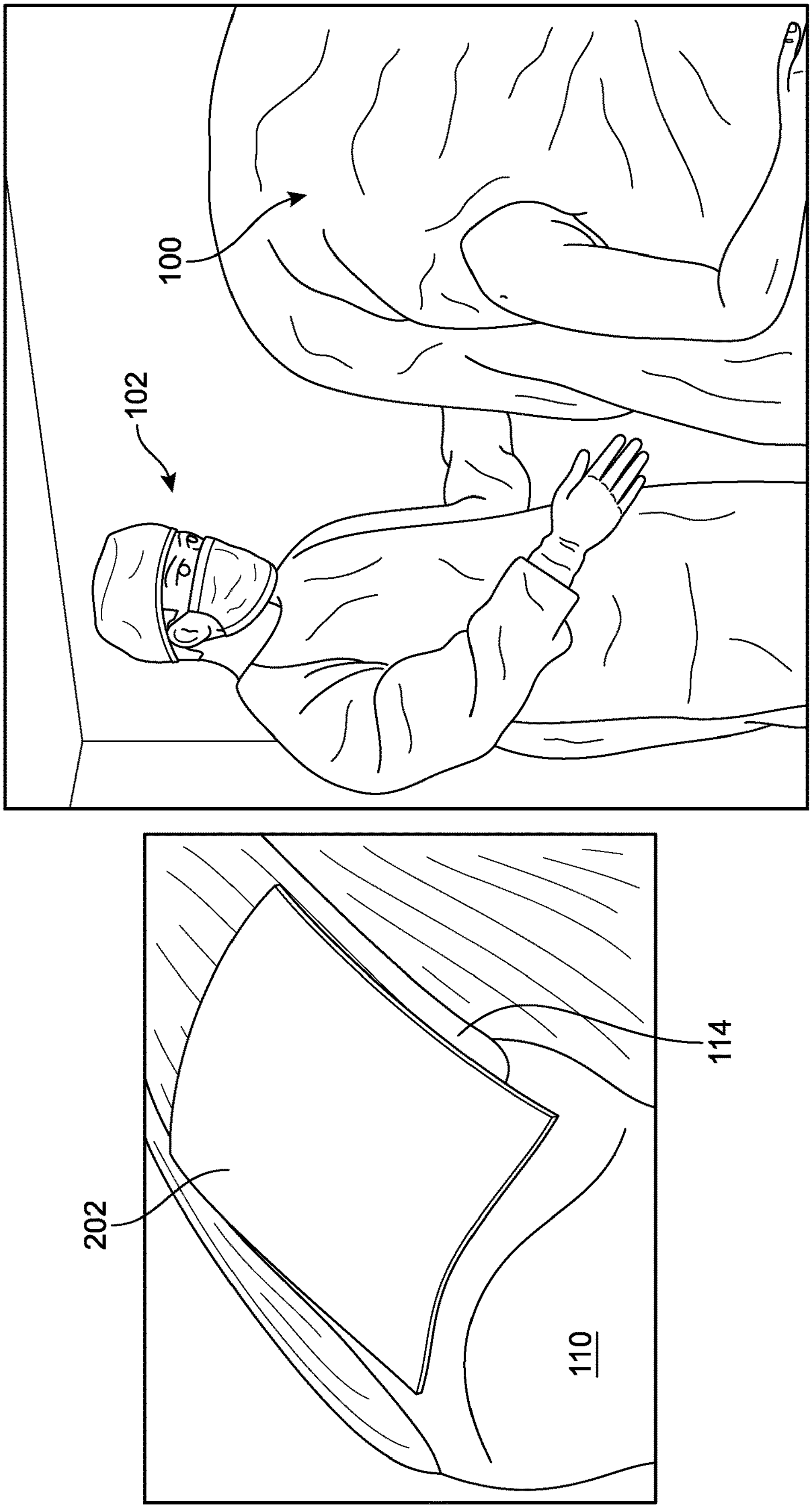
FIG. 2 is a schematic view of a step of applying an implant to a portion of a rotator cuff tendon to facilitate healing according to an embodiment.

Once the tendon has been sufficiently repaired and/or the surgical site is otherwise prepared, surgeon 102 may insert an implant, such as a graft, through an incision (possibly using another device to facilitate insertion). The graft can then be placed over the tendon and/or portion of the underlying bone in order to facilitate healing. As an example, FIG. 2 shows a schematic view of a graft 202 that has been applied over the tendon 114 as well as over a portion of humerus 110.

Although the exemplary embodiment depicts a procedure in which a tendon is first secured to the bone using sutures and anchors, in other embodiments a graft can be applied to one or more tendons without first reattaching a tendon. For example, grafts could be applied to tendons that have only partial tears.

Once graft 202 has been placed over the tendon, one or more sutures or anchors are required to hold graft 202 in place. The present embodiments disclose a graft delivery device configured to hold an implant, such as a graft, during insertion and release the implant/graft once it has been secured at the surgical site.

An embodiment of an implant delivery device that can be used to insert an implant through a small incision and position it in over tissue in a fully opened condition is shown in FIGS. 3-19.

The implant delivery device may include provisions for biasing a sheetlike implant to an open, unfurled configuration as well as for releasing the implant once it has been placed in a desired location. The handle includes provisions to actuate components of an implant holding portion of the device. It will be understood that the disclosed implant delivery device may be configured to deliver any type of sheet-like implant. For example, in some embodiments, the delivery device may be used to deliver a sheet-like graft. In some embodiments, the graft may be formed, at least in part of collagen. In other embodiments, the sheet-like implant may be formed of synthetic material or blends of collagen and various synthetic polymers as are described, for example, in Francis et al., U.S. Pat. No. 10,617,787, issued Apr. 14, 2020, and entitled "Biopolymer Compositions, Scaffolds and Devices," the entire disclosure of which is incorporated herein by reference, and Francis et al., U.S. Pat. No. 10,653,817, issued May 19, 2020, and entitled "Method for Producing an Implantable Ligament and Tendon Repair Device," the entire disclosure of which is incorporated herein by reference.

The handle includes a slider member coupled to components that facilitate releasing the implant once it has been placed in a desired position in the body of the patient. The slider member and related components are described in further detail below and shown.

The deployment device may be designed to be easily held. To this end, the body may include a handgrip portion. The handgrip portion may be designed to accommodate either a left or right hand. A user's hand may engage the handgrip portion and use their fingers to actuate the slider member. Additionally, a user's finger(s) or thumb can be used to move the slider member. It may be appreciated that in some embodiments, a variety of different materials, coatings and/or surface treatments can be used with the handle and/or the slider member to improve grip and prevent slipping.

In some embodiments, the disclosed implant delivery device may be configured for insertion through a medical cannula. Medical cannulas are generally well-known in the art of arthroscopic surgery. For example, various types of cannulas are used to control the inflow or outflow of fluids, to allow access for tools into the tissue, and for other functions. In some types of surgeries, an implant or other substrate material may be introduced into a surgical site through a cannula, which maintains an enlarged access port to the surgical site. Additionally, many arthroscopic surgeries, such as joint surgeries, use pressurized irrigation fluid to keep tissue separated apart from other tissue. In particular, pressurized irrigation fluid may be used to aid in visualization of the surgical site as well as to prevent bleeding from vasculature surrounding the surgical cuts. Other types of surgeries, such as gastrointestinal procedures, use pressurized gas to provide access to and visualization of the surgical site.

Utilizing a cannula eliminates the need to include an outer sheath covering the implant during insertion. That is, if the implant is inserted through an incision in the bare skin of the patient, the implant, which is typically relatively delicate, is typically preferred to be encased. Accordingly, implant delivery devices configured to introduce implants directly through the skin (i.e., without a cannula) typically include a sheath that covers the implant during insertion and which is then retracted to expose the implant once the distal end of the instrument reaches the surgical site. Alternatively, devices may include a fixed outer sheath and a movable inner component that holds the implant within the sheath during insertion and is then moved distally to expose the implant at the surgical site.

The presently disclosed implant delivery device is devoid of implant-covering sheathes. Instead, the disclosed device includes resilient implant supporting flange members that pinch the implant generally along a midline of the implant. The flange members abut against a partial area of both sides of the implant. The resilient flange members thus bias the implant toward an unfurled configuration. However, because both the implant and flange members are flexible, the implant (and flange members) may roll up when delivered through a surgical cannula. When the distal end of the device exits the distal end of the cannula, the flange members bias the implant into an unfurled condition. The implant can then be positioned over the tendon and/or bone at the surgical site. In addition, the implant delivery device can be used to hold the implant in place while anchors are used to secure the implant to the native tissue/bone.

Figure 3:
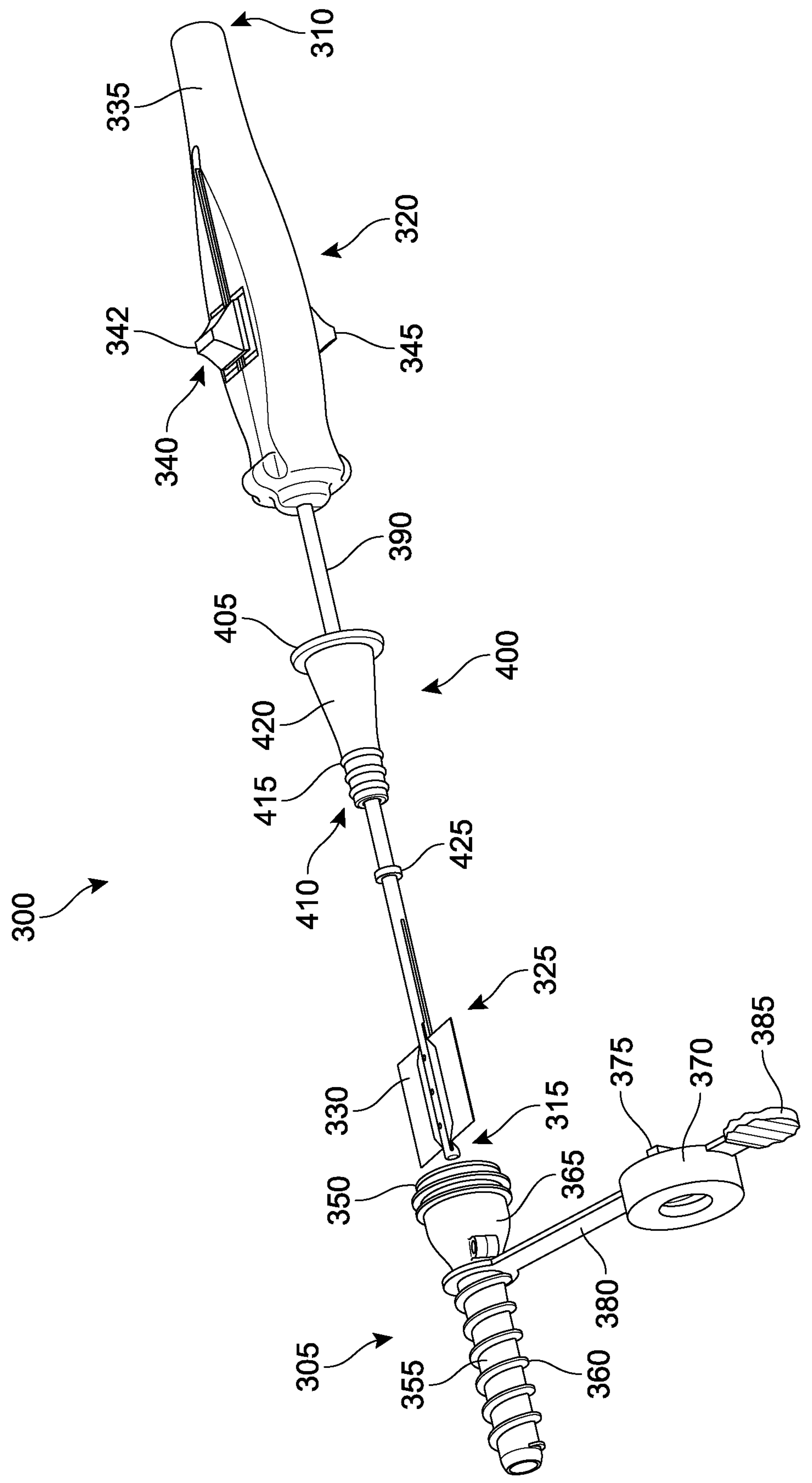
FIG. 3 is a schematic illustration of an implant delivery device according to an embodiment holding an implant prior to delivery through an illustrated access cannula.

FIG. 3 is a schematic illustration of an implant delivery device according to an embodiment holding an implant prior to delivery through an illustrated access cannula. As shown in FIG. 3, an implant delivery device 300 may be configured to be inserted through a cannula 305. As further shown in FIG. 3, implant delivery device 300 may have a proximal end 310 and a distal end 315. In addition, implant delivery device 300 may include a handle 320 disposed at proximal end 310 of implant delivery device 300 and configured to be grasped by a user.

Implant delivery device 300 may include an implant holding portion 325 proximate distal end 315 of implant delivery device 300, implant holding portion 325 being configured to retain a sheet-like implant 330 during implantation of implant 330.

Handle 320 may include a casing 335 including a slider member 340 configured to actuate an implant release mechanism discussed in greater detail below. In some embodiments, handle 320 may include an ambidextrous configuration. For example, as shown in FIG. 3, slider member 340 may include a first slider 342 and a second slider 345. As shown in later FIGS. (see, e.g., FIG. 18), first slider 342 may be attached to or integral with second slider 345. Thus, actuating either slider will have the same effect. Accordingly, a surgeon can use either hand and hold the device in a variety of orientations and still have ready access to slider member 340.

Casing 335 of handle 320 may be formed of a substantially rigid material, such as a hard/rigid plastic and/or metal. Casing 335 must substantially maintain its shape and structural integrity during manipulation of implant delivery device 300 as handle 320 is the portion of the device to which forces are applied during use. Further, the connection between handle 320 and outer shaft 390 must be configured to withstand this loading.

As shown in FIG. 3, exemplary cannula 305 may have a proximal end 350 with a wider mouth opening and a narrower distal portion 355 including threads 360. Cannula 305 may include a tapered intermediate portion 365 between proximal end 350 and distal portion 355. Implant delivery device 300 may be configured such that, when passing implant 330 through cannula 305, tapered intermediate portion 365 may roll up implant 330. As further shown in FIG. 3, cannula 305 may include a seal structure 370. Seal structure may include a seal 375. Seal 375 may be any type of seal suitable for passing instruments, such as obturators through. For example, as shown in the accompanying figures, seal 375 may be a duckbill valve. In other embodiments, seal 375 may be a tricuspid valve. In some embodiments, seal structure 370 may include more than one seal in series. In addition, seal structure 370 may include a tether 380 for connecting seal structure 370 to cannula 305. Further, seal structure 370 may include a grasping tab 385. It will be understood that cannula 305 and seal structure 370 may have any suitable configurations for passing implants therethrough using implant delivery device 300. Implant delivery device 300 may be configured for use with cannulas having any of the features disclosed in Jones et al., U.S. patent application Ser. No. 17/173,531, filed Feb. 11, 2021, and entitled "Surgical Cannula with Removable Pressure Seal," the entire disclosure of which is incorporated herein by reference.

Further, implant delivery device 300 may include an outer shaft 390 extending from handle 320 to distal end 315 of implant delivery device 300. Outer shaft 390 may be formed out of a substantially rigid material that is also biocompatible. For example, outer shaft 390 may be formed out of surgical stainless steel or titanium. In some embodiments, outer shaft 390 may be formed to have substantially no deflection when subjected to the forces of implant delivery. In other embodiments, outer shaft 390 may be configured to have a predetermined amount of flexibility in order to facilitate placement of the implant via manipulation of the handle. It will be understood that, also contemplated are configurations where the implant is not necessarily attached to a shaft, but attached to an alternative structure at the distal end of the device.

In addition, as shown in FIG. 3, implant delivery device 300 may further include a cannula sealing member 400 disposed about a midportion of outer shaft 390. Cannula sealing member 400 may include a proximal flange 405 for abutting proximal end 350 of cannula 305. In addition, cannula sealing member 400 may include a narrower distal portion 410 configured to fit within narrow distal portion 355 of cannula 305. Distal portion 410 of cannula sealing member 400 may include one or more ribs 415 configured to seal against the inner wall of distal portion 355 of cannula 305. In addition, cannula sealing member 400 may include a tapered intermediate portion 420 between proximal flange 405 and narrow distal portion 410.

When implant insertion device 300 is to be inserted through cannula 305, seal structure 370 may be removed from proximal end 350 of cannula 305. In order to maintain pressure at the surgical site, cannula sealing member 400 may be inserted into cannula 305 as implant delivery device 300 is passed through cannula 305. Cannula sealing member 400 may be slidable along outer shaft 390 of implant insertion device 300 in order to facilitate manipulation of implant insertion device 300 to and about the surgical site.

As also shown in FIG. 3, outer shaft 390 of implant delivery device 300 may include a ring 425 disposed distal to cannula sealing member 400 and configured to pull cannula sealing member 400 out of cannula 305 when handle 320 of implant delivery device 300 is pulled in the proximal direction to withdraw implant delivery device 300 from the surgical site.

Figure 4:
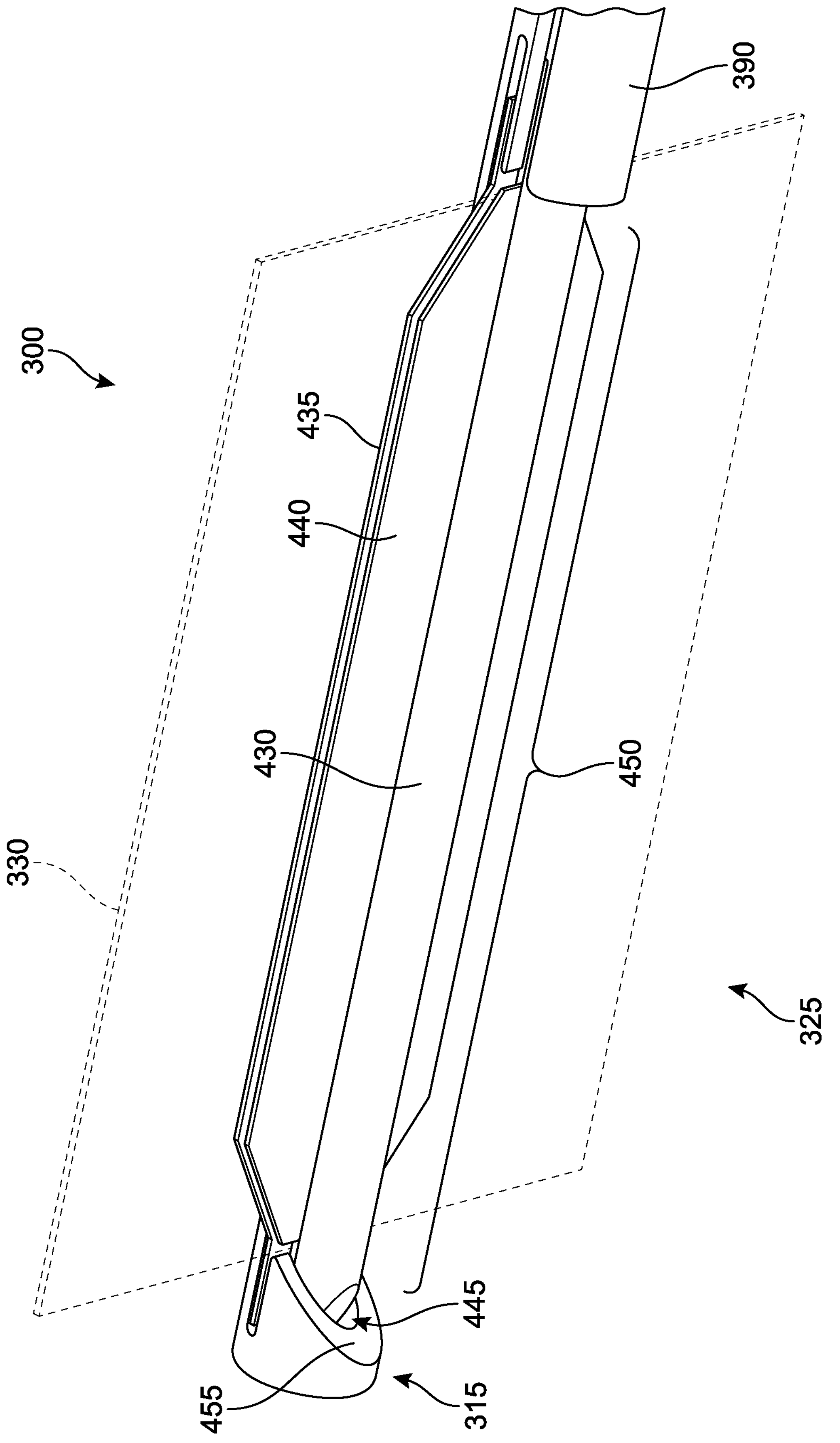
FIG. 4 is an enlarged schematic view of an implant holding portion of the implant delivery device holding an implant.

FIG. 4 is an enlarged schematic view of an implant holding portion of the implant delivery device holding an implant. In particular, as shown in FIG. 4, implant holding portion 325 may include a recess 450 configured to receive implant 330, a fixed implant supporting flange member 435 disposed within recess 450 and configured to support implant 330 on one side, and a movable implant supporting flange member 440. Fixed implant supporting flange member 435 may be fixedly attached to outer shaft 390 within recess 450. Movable implant supporting flange member 440 may be configured to be slidable between a first, distal position and a second, proximal position. In the first, distal position, movable implant supporting flange member 440 is disposed within recess 450 and secures implant 330 against fixed implant supporting flange member 435, thus holding implant 330 in recess 450 in an unfurled configuration, as shown in FIG. 4. It will be noted that, although the flange members are not as large as the implant, the partial support provided by the smaller flange members is enough to maintain the implant in a substantially unfurled condition. Depending on the type of implant with which the device is to be used, and the relative stiffness of the implant, the flange members may vary in stiffness and/or size. In addition, the distance between the flange members may vary depending on the thickness of the implant and the relative compressibility of the implant in order to ensure suitable clamping force between the flange members.

Fixed implant supporting flange member 435 and movable implant supporting flange member 440 may be formed of a flexible but resilient material. That is, the material may be able to flex relatively easily, but return to the flat configuration when the loading is removed.

In addition, since fixed implant supporting flange member 435 and movable implant supporting flange member 440 are exposed to the surgical site, they may be formed of a biocompatible material. Such biocompatible plastics may include the following: polyethylene, polypropylene, polyimide (Kapton®), acrylonitrile butadiene styrene and PAEK polymers. In some embodiments, implant supporting flange members formed of such materials may have thicknesses of approximately 0.001 to 0.025 inch. Other possible materials for the flange members may include nitinol, stainless steel, and/or titanium. Implant supporting flange members formed of such metallic materials may be formed in the appropriate thickness to match the properties of flange members formed of the non-metal materials mentioned above.

As also shown in FIG. 4, movable implant supporting flange member 440 may be attached to an inner shaft 430, which may be translated in the proximal and distal directions to slide movable implant supporting flange member 440. Further, distal end 315 of implant delivery device 300 may include a recess 445 at the end of outer shaft 390 for receiving a distal tip of inner shaft 430. Since at least a portion of inner shaft 430 is exposed to the surgical site, inner shaft 430 may also be formed of a biocompatible material, such as surgical stainless steel or titanium.

In addition, as also shown in FIG. 4, a distal wall 455 of recess 450 may be beveled. This bevel may facilitate release of implant 330, and removal of implant delivery device 300 from the surgical site as it is withdrawn across a delivered implant. That is, when removing implant delivery device 300, the bevel of distal wall 455 may enable outer shaft 390 to slide past implant 330 without catching on an edge of implant 330.

Figure 5:
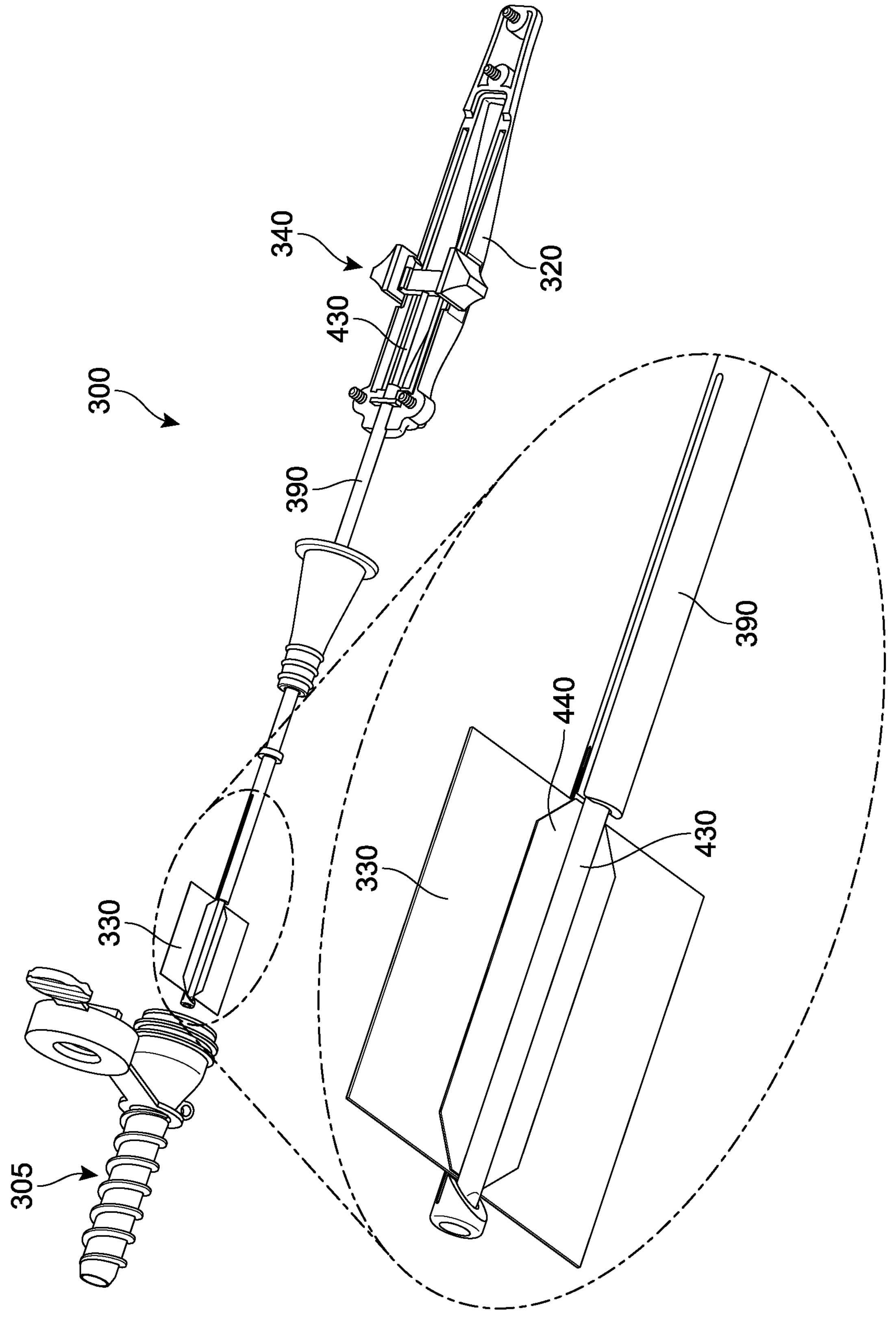
FIG. 5 is another schematic view of an implant delivery device according to an embodiment holding an implant prior to delivery through an illustrated access cannula.

FIG. 5 is another schematic view of implant delivery device 300 holding implant 300 prior to delivery through cannula 305. Panel 335 (FIG. 3) is removed in FIG. 5 in order to expose the inner mechanics of handle 320. Slider member 340 may be configured to be moved in the proximal and distal directions in order to slide movable implant supporting flange member 440 between the first, distal position discussed above and shown in FIG. 5 (as well as FIGS. 3 and 4) and a second, proximal position (shown in FIG. 16 and discussed in further detail below) wherein movable implant supporting flange member 440 is withdrawn from the recess in outer shaft 390 (see recess 445, shown in FIG. 4), thus enabling release of implant 330 from the recess.

It will be understood that, in some embodiments, the sliding movement of the movable implant supporting flange member may be opposite. That is, the movable flange member may be slid in the distal direction to release the implant. In still other embodiments, the movable implant supporting flange member may be moved in an alternative non-sliding manner to release the implant. For example, in some embodiments, the movable implant supporting flange member may be moved with respect to the fixed implant supporting flange member in a clamshell type action. In some cases, the clamshell opening may occur at the proximal end or distal end of the implant. In other cases, the clamshell opening may be at one lateral side of the implant or the other.

FIG. 5 also includes an enlarged view of the implant holding portion of implant delivery device 300. In this view, FIG. 5 shows movable implant supporting flange member 440 disposed against implant 330, preventing implant 330 from being released. FIG. 5 also shows inner shaft 430 extending through outer shaft 390 and connecting slider member 340 in handle 320 to movable implant supporting flange member 440 at the distal end of implant delivery device 300.

Figure 6:
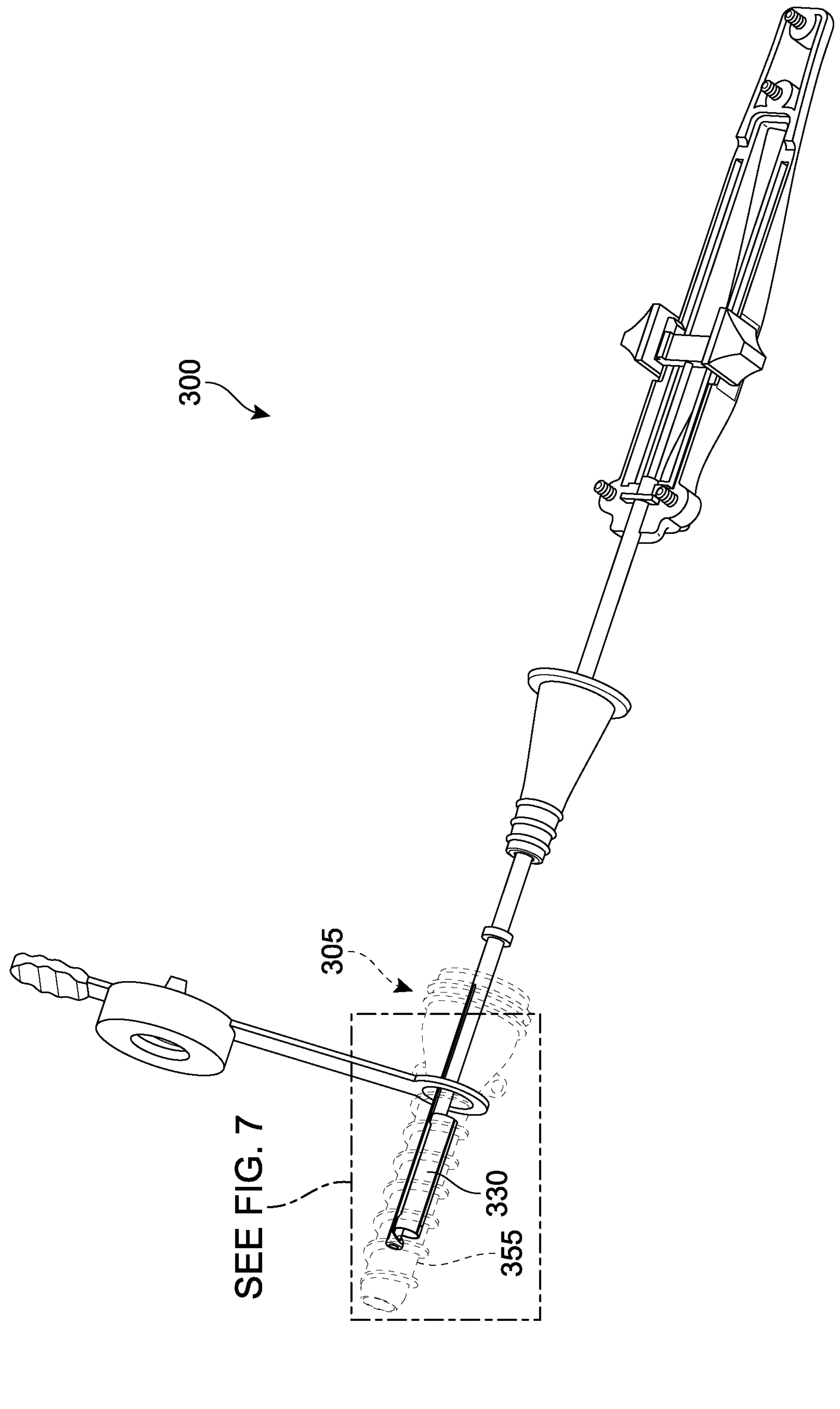
FIGS. 6-7 are schematic views showing the implant being inserted through the cannula.
Figure 7:
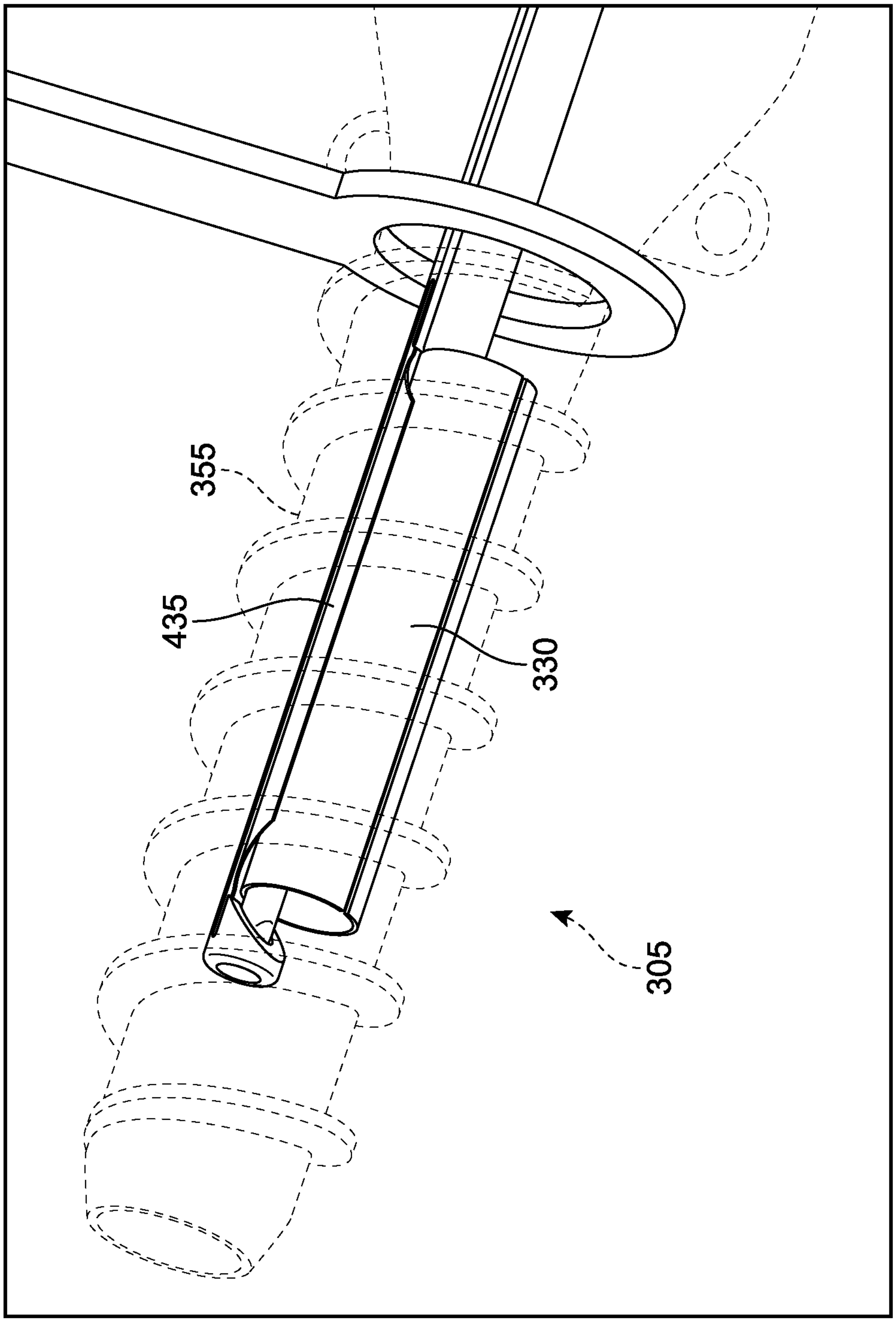

FIGS. 6-7 are schematic views showing the implant being inserted through the cannula. FIG. 6 shows cannula 305 in phantom in order to reveal the implant holding portion of implant delivery device 300 along with implant 330 being passed through cannula 305. As shown in FIG. 6, and more clearly shown in FIG. 7, implant 330 may roll up when being passed through cannula 305.

It will be understood that the fixed implant supporting flange member (435; FIG. 4) and the movable implant supporting flange member (440; FIG. 4) are flexible and resilient such that the fixed implant supporting flange member and the movable implant supporting flange member may be collapsed/deflected upon delivery through cannula 305. In some cases, as shown in FIG. 7, the flange members and implant 330 may roll up in order to facilitate passage of implant 330 through cannula 305 and to provide protection for implant 330 during this passage. It will be understood, however, that the implant and the flange members may fold, wrinkle, or otherwise collapse in a uniform or non-uniform manner upon insertion through the cannula. In other words, the implant and the flange members may have a constrained condition or form in which these elements are at least partially collapsed, and an unconstrained condition or form in which these elements are substantially unfurled. The collapsed/constrained condition may occur in situ, as the surgeon passes the distal end of the delivery device with the implant through a cannula. This collapsed/constrained condition may be a “non-use” condition of the implant, whereas the (substantially) unfurled condition may be a “use” condition.

Figure 8:
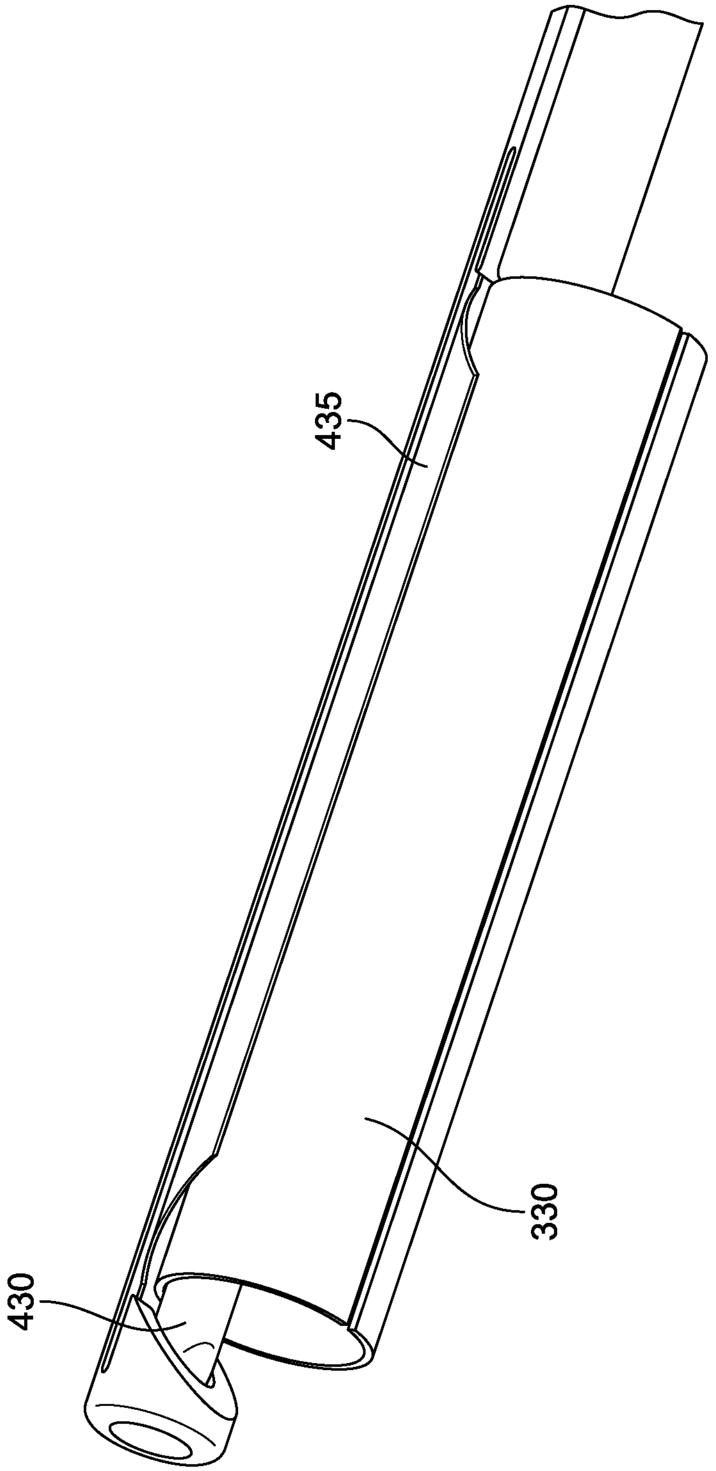
FIG. 8 is a schematic view of the implant being rolled up as it is during delivery through the cannula, but with the cannula removed for purposes of illustration.

FIG. 8 is a schematic view of the implant being rolled up as it is during delivery through the cannula, but with the cannula removed for purposes of illustration. As shown in FIG. 8, not only is implant 330 collapsed, but fixed implant supporting flange member 435 is also collapsed along with implant 330. Although inside the collapsed implant 330, movable implant supporting flange member (440) is also collapsed.

Figure 9:
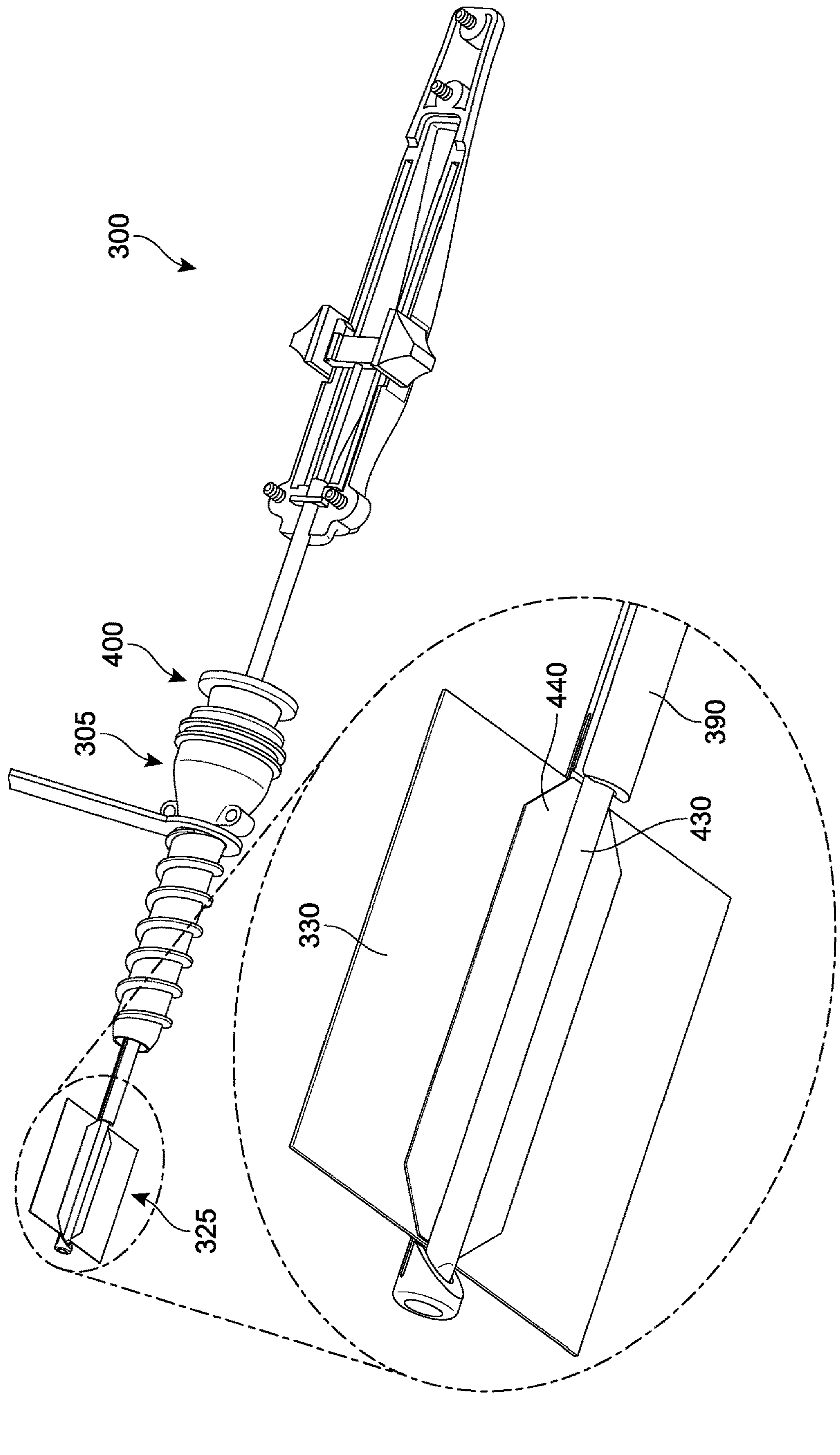
FIG. 9 is a schematic view of the implant delivery device extending through the cannula with the cannula sealing member seated within the cannula and with the implant unfurled after exiting the cannula.

FIG. 9 is a schematic view of the implant delivery device extending through the cannula with the cannula sealing member seated within the cannula and with the implant unfurled after exiting the cannula. In particular, FIG. 9 shows implant holding portion 325 of implant delivery device 300 extending beyond the distal end of cannula 305. Accordingly, implant 330 is unfurled in this position, since the cannula is no longer surrounding implant 330 to keep it rolled up.

FIG. 9 also shows cannula sealing member 400 seated within cannula 305. In this configuration of the components, pressure may be maintained within the surgical site and the implant is ready to be anchored to the tissue/bone and then released from implant holding portion 325 of implant delivery device 300.

Figure 10:
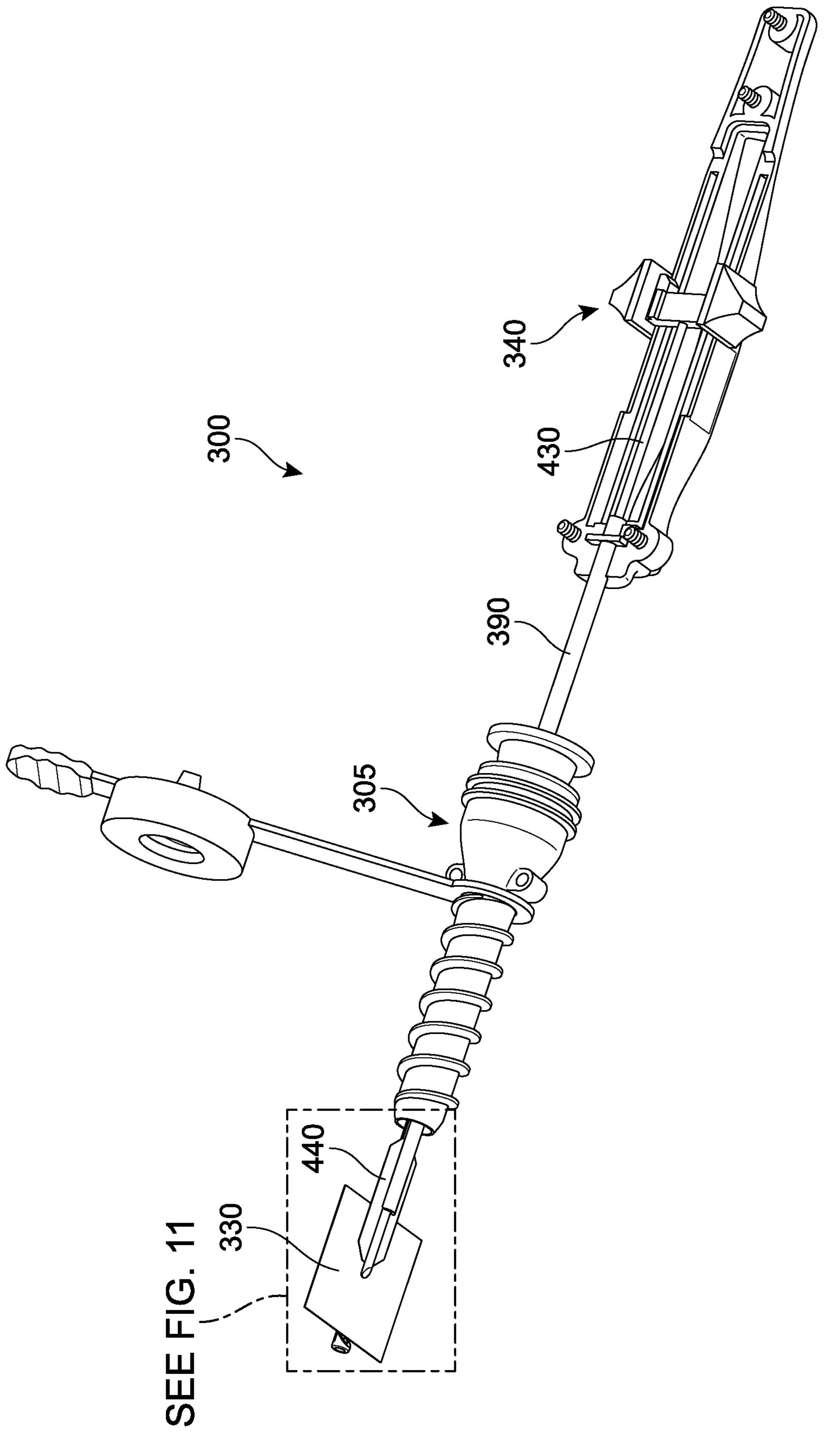
FIG. 10 is a schematic view of the implant delivery device with an implant supporting flange member partially withdrawn part way through the process of releasing the implant.

FIG. 10 is a schematic view of the implant delivery device with an implant supporting flange member partially withdrawn part way through the process of releasing the implant. As shown in FIG. 10, slider 340 has been moved proximally a portion of its permitted travel. Accordingly, inner shaft 430 has moved proximately, thus sliding the attached movable implant supporting flange member 440 in the proximal direction. It will be noted that there are not necessarily any detents that stop the mechanism at this stage of withdrawal. This is an intermediate condition illustrated simply to facilitate demonstration of the process of withdrawing movable implant supporting flange member 440.

Figure 11:
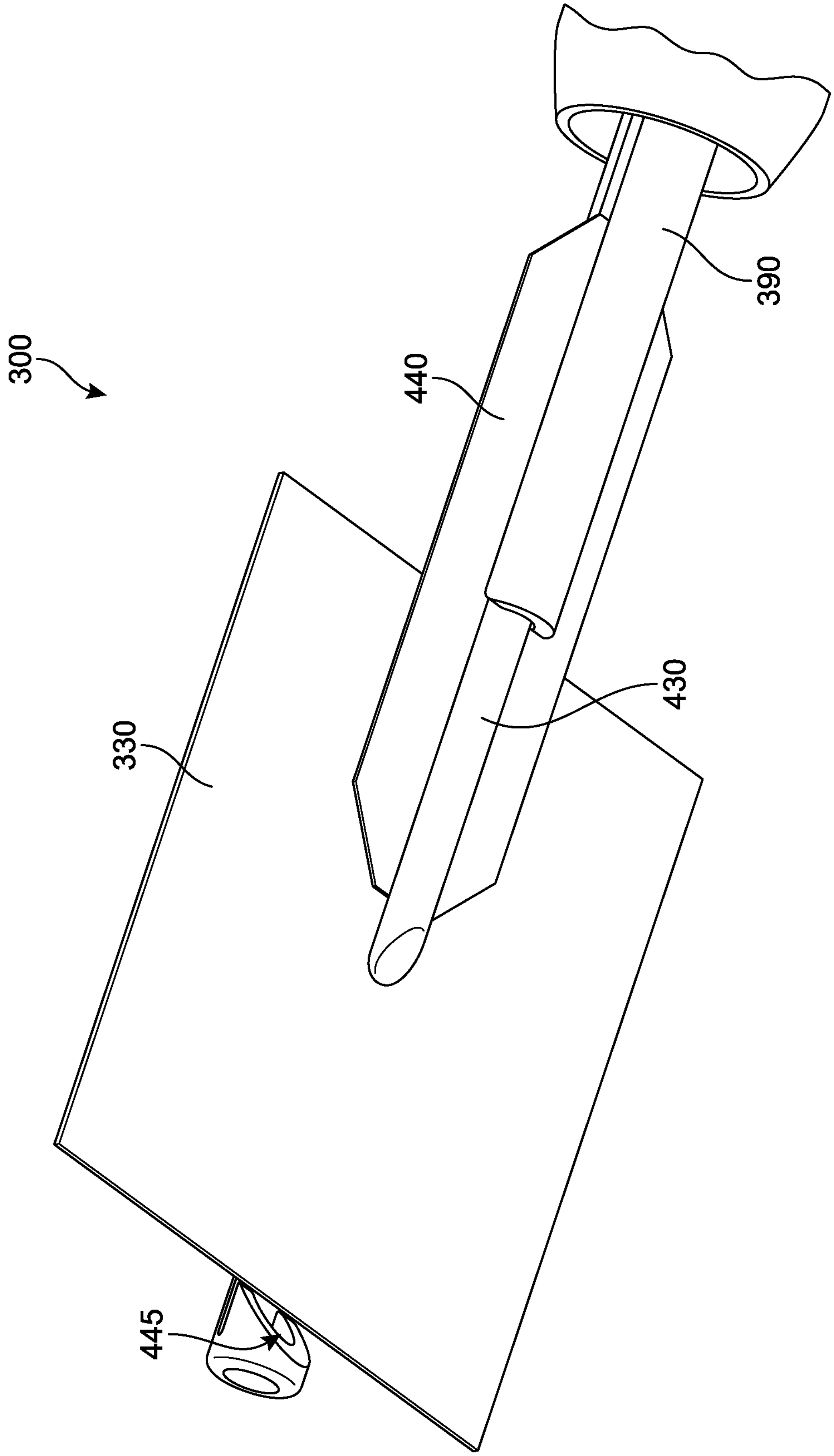
FIG. 11 is an enlarged schematic view of the implant holding portion of the implant delivery device with the implant supporting flange member partially withdrawn, as shown in FIG. 10.

FIG. 11 is an enlarged schematic view of the implant holding portion of the implant delivery device with the implant supporting flange member partially withdrawn, as shown in FIG. 10. As illustrated in FIG. 11, inner shaft 430 is partially withdrawn, as is movable implant supporting flange member 440 attached thereto. In this condition, the distal half of implant 330 is no longer supported on both sides. Again, this intermediate condition is merely shown for purposes of illustrating the translation of movable implant supporting flange member 440.

Figure 12:
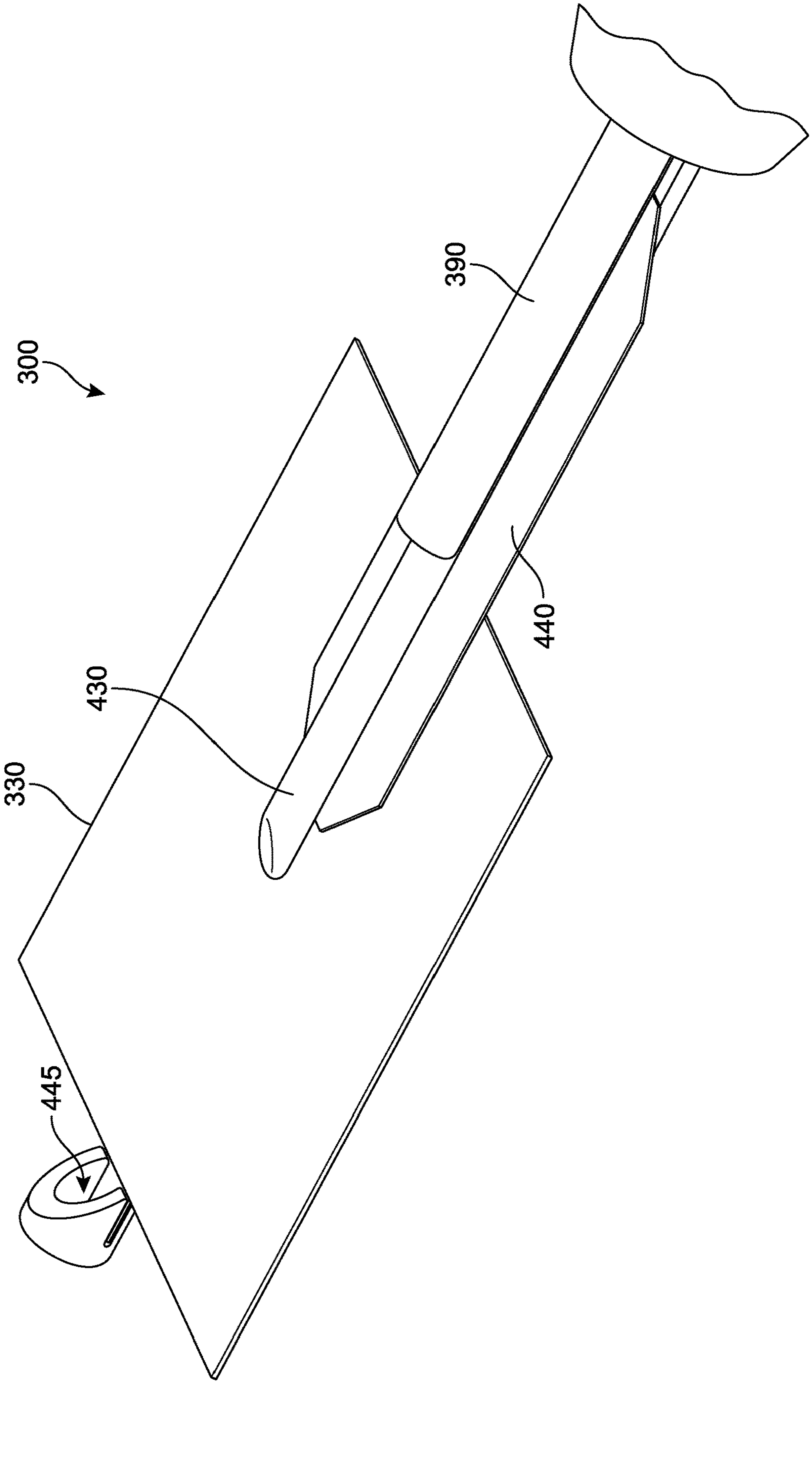
FIG. 12 is another enlarged schematic view of the implant holding portion of the implant delivery device with the implant supporting flange member partially withdrawn.

FIG. 12 is another enlarged schematic view of the implant holding portion of the implant delivery device with the implant supporting flange member partially withdrawn. FIG. 12 shows recess 445 into which the distal end of inner shaft 430 is disposed when movable implant supporting flange member 440 is in the distal (i.e., implant holding) position.

Figure 13:
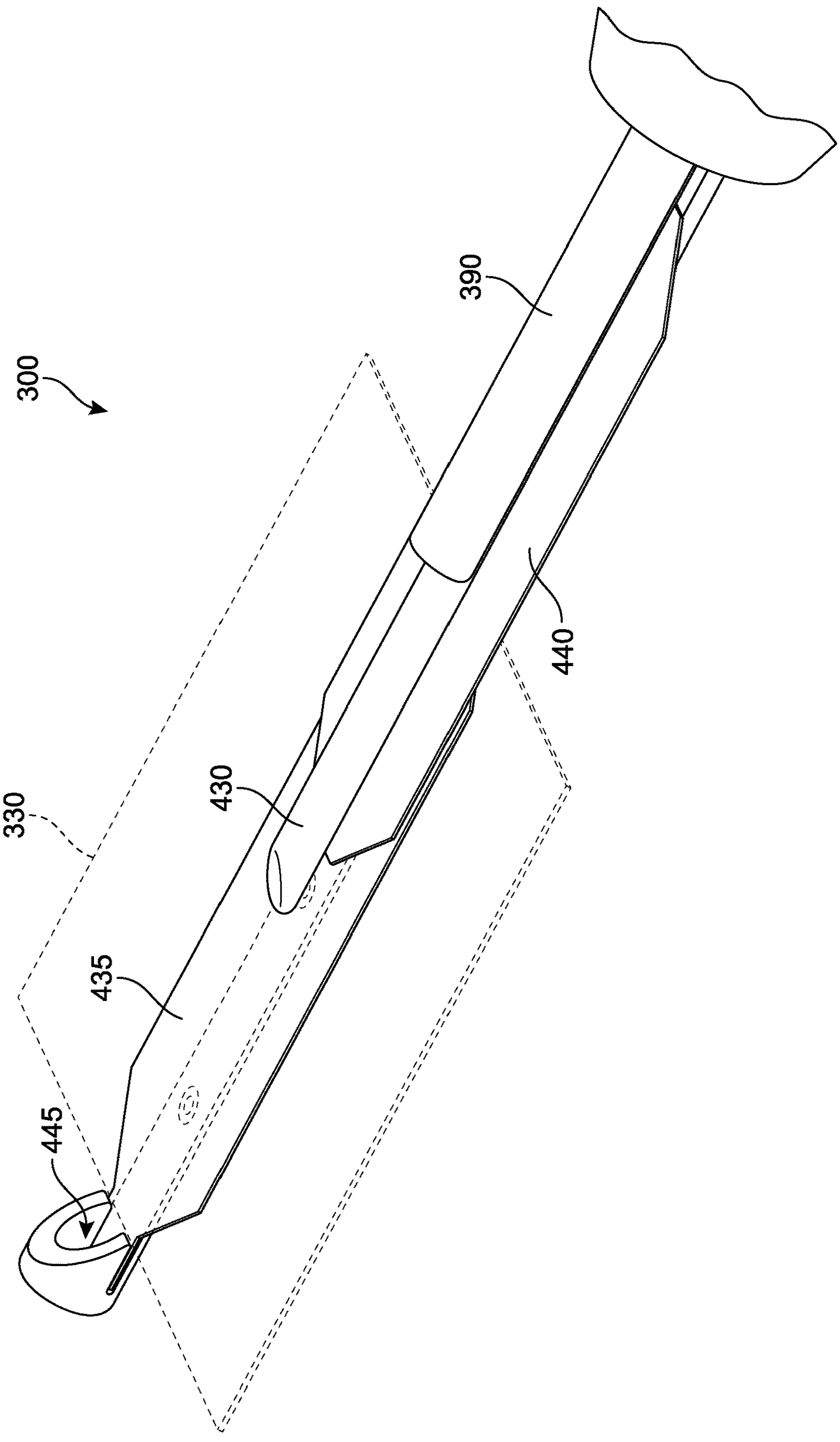
FIG. 13 is another enlarged schematic view of the implant holding portion of the implant delivery device with the implant supporting flange member partially withdrawn and with the implant shown in phantom in order to illustrate a second implant supporting member under the implant.

FIG. 13 is another enlarged schematic view of the implant holding portion of the implant delivery device with movable implant supporting flange member 440 partially withdrawn and with implant 330 shown in phantom in order to illustrate fixed implant supporting member 435 under implant 330. FIG. 13 illustrates how fixed implant supporting flange member 435 remains in place, fixed to outer shaft 390 and movable implant supporting flange member 440 has been moved proximally relative to fixed implant supporting flange member 435.

Figure 14:
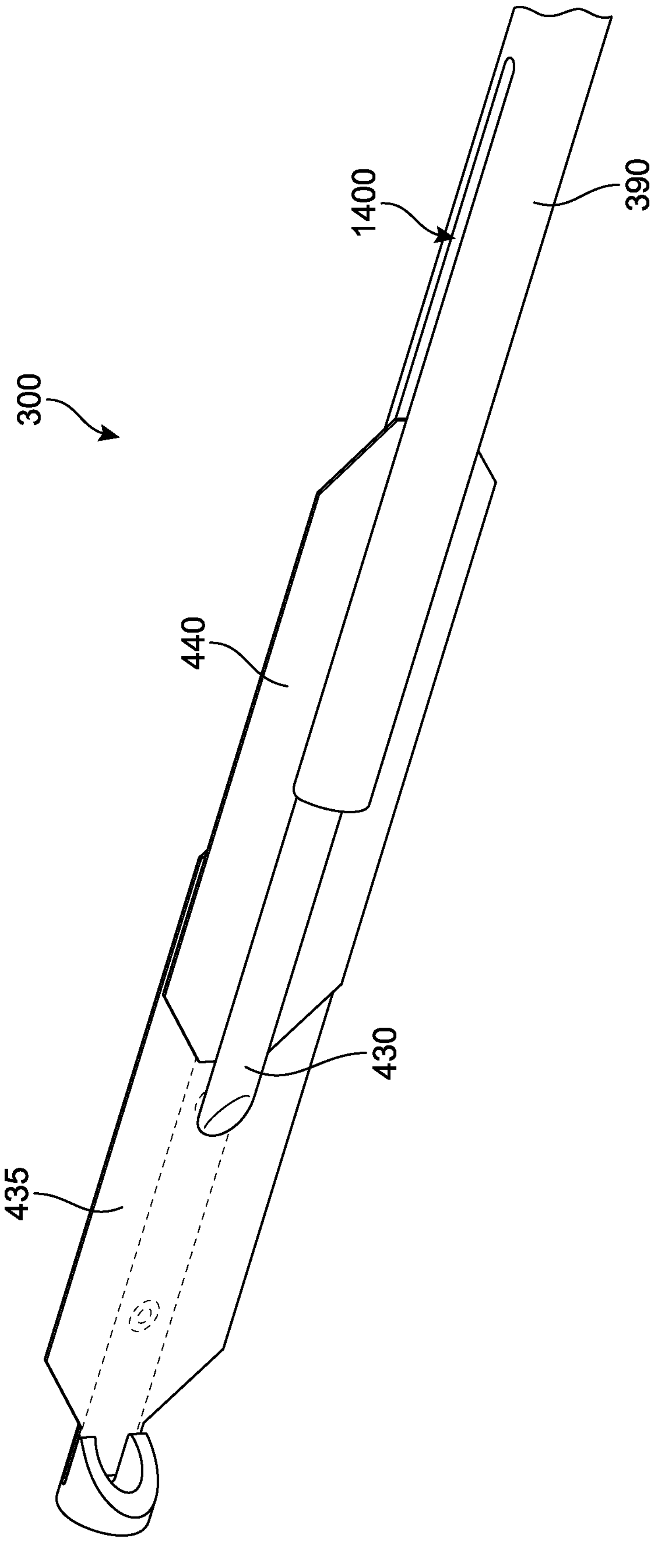
FIG. 14 is an enlarged schematic view of the implant holding portion of the implant delivery device with the implant supporting flange member partially withdrawn and with the implant omitted in order to illustrate the relationship between the two implant supporting flange members.

FIG. 14 is an enlarged schematic view of the implant holding portion of the implant delivery device with the implant supporting flange member partially withdrawn and with the implant omitted in order to illustrate the relationship between the two implant supporting flange members. Again, fixed implant supporting flange member 435 remains in place at the distal end of implant delivery device 300 and movable implant supporting member 440 has been moved proximally relative to fixed implant supporting flange member 435 and outer shaft 390. In order to facilitate this movement of movable implant supporting flange member 440, outer shaft 390 may include a slot 1400. As shown in FIG. 14, outer shaft 390 may include slot 1400 into which movable implant supporting flange member 440 is slid when inner shaft 430 is moved in the proximal direction.

Figure 15:
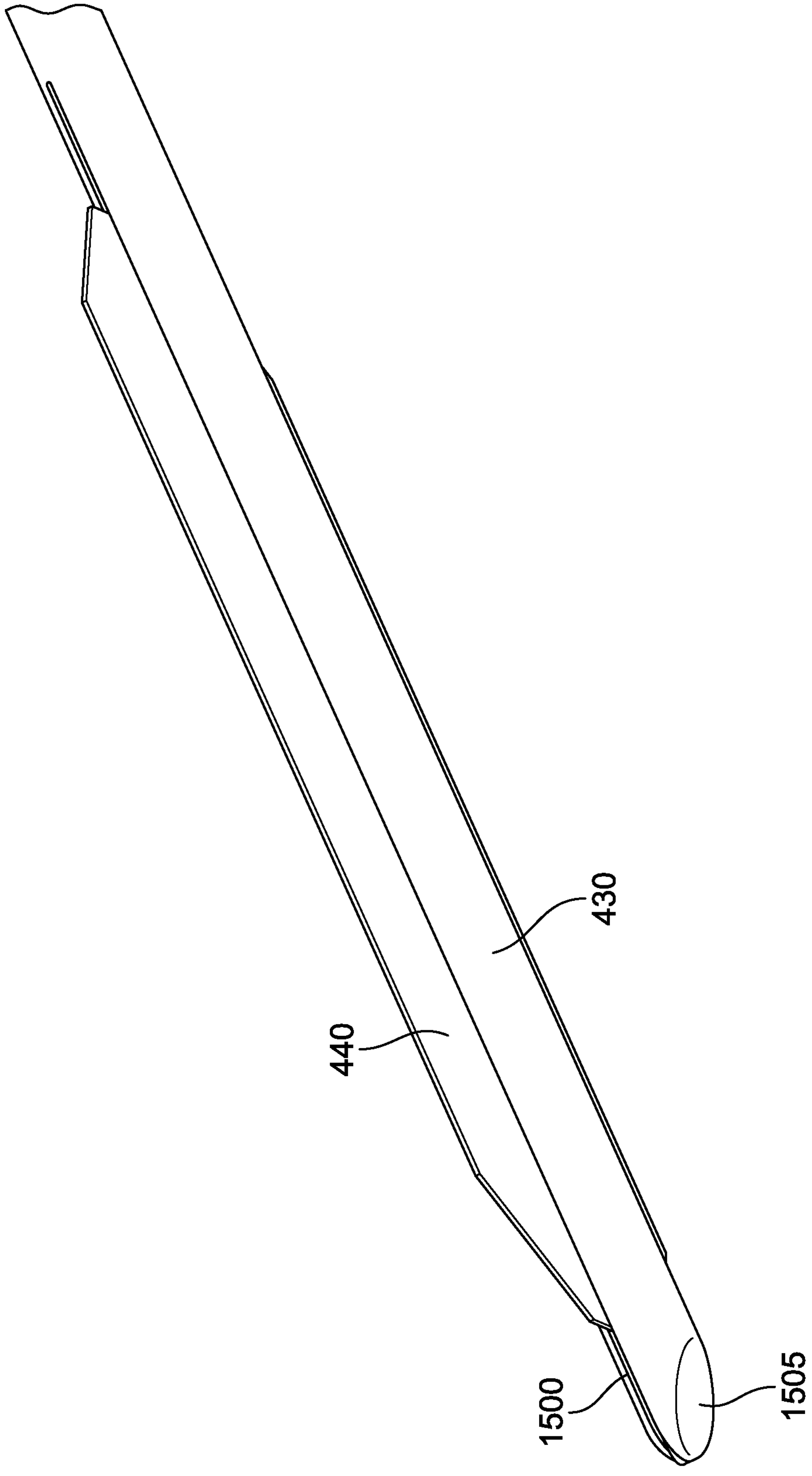
FIG. 15 is a schematic views of an inner shaft and a movable implant supporting flange member held therein.

FIG. 15 is a schematic views of an inner shaft and a movable implant supporting flange member held therein. As shown in FIG. 15, inner shaft 430 may include a slit 1500 in which movable implant supporting flange member 440 is disposed. Movable implant supporting flange member 440 may be snugly fitted within slit 1500 so that movable implant supporting flange member 440 moves when inner shaft 430 is moved. In addition, the distal tip of inner shaft 430 may include a beveled end 1505 in order to facilitate insertion of this distal tip into the recess (445; FIG. 4) at the distal end of outer shaft 390.

Figure 16:
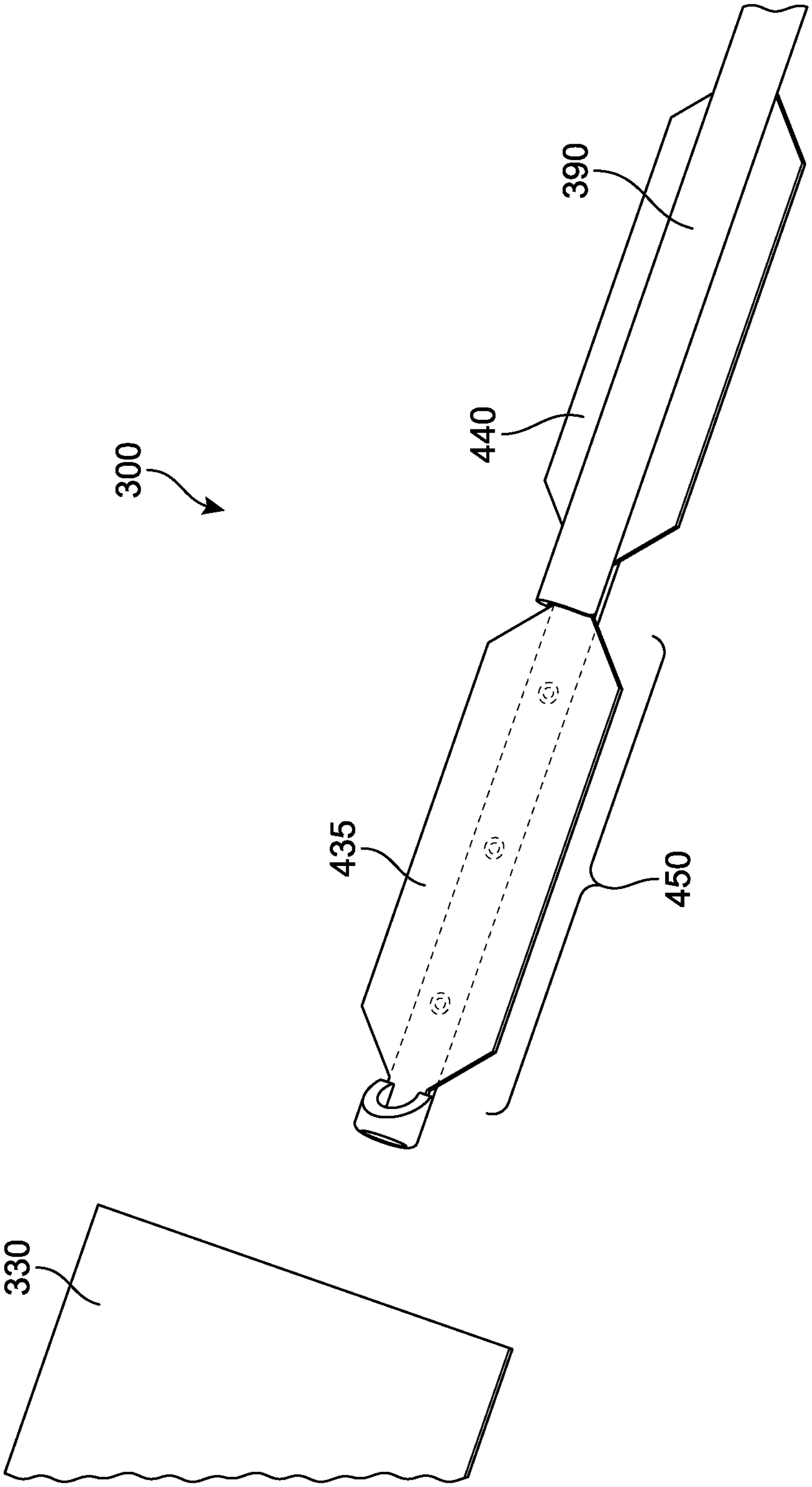
FIG. 16 is a schematic view of the implant holding portion of the implant delivery device with the implant supporting flange member fully withdrawn and with the implant released from the implant delivery device.

In order to fully release the implant from the recess in the outer shaft, the inner shaft is retracted further, completely withdrawing the movable implant supporting flange member from the recess. FIG. 16 is a schematic view of the implant holding portion of the implant delivery device with the implant supporting flange member fully withdrawn and with the implant released from the implant delivery device. A shown in FIG. 16, movable implant supporting flange member 440 has been moved further proximally and no longer overlaps with fixed implant supporting flange member 435. Accordingly, implant 330 is released from recess 450 in outer shaft 390 of implant delivery device 300.

Figure 17:
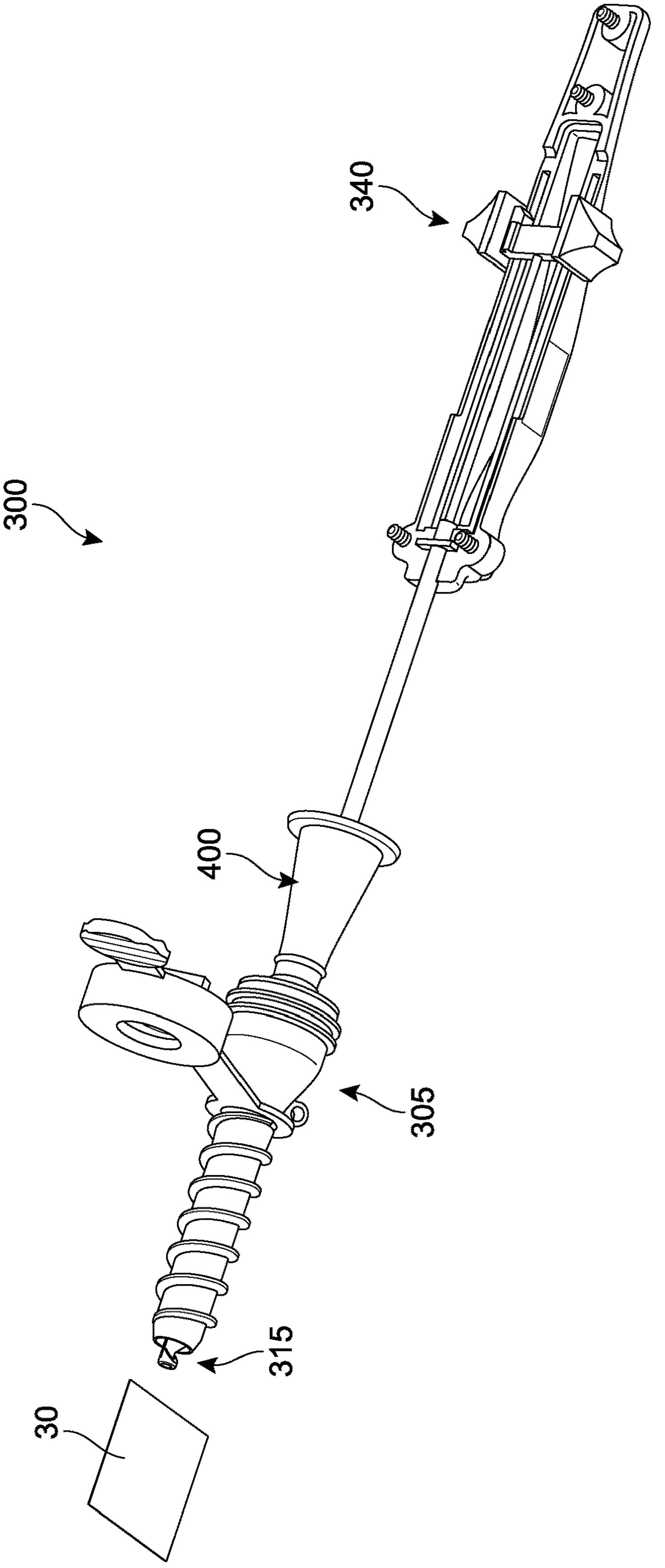
FIG. 17 is a schematic view of the implant delivery device being withdrawn through the cannula after having delivered the implant.

Once implant 330 is secured at the surgical site and released, implant delivery device 300 may be removed from the surgical site through cannula 305. FIG. 17 is a schematic view of implant delivery device 300 being withdrawn through cannula 305 after having delivered implant 330. FIG. 17 further shows slider member 340 in its most proximal location having been slid proximally to fully retract the movable implant supporting flange member (440; FIG. 16). In addition, FIG. 17 also shows cannula sealing member 400 partially withdrawn from cannula 305.

Figure 18:
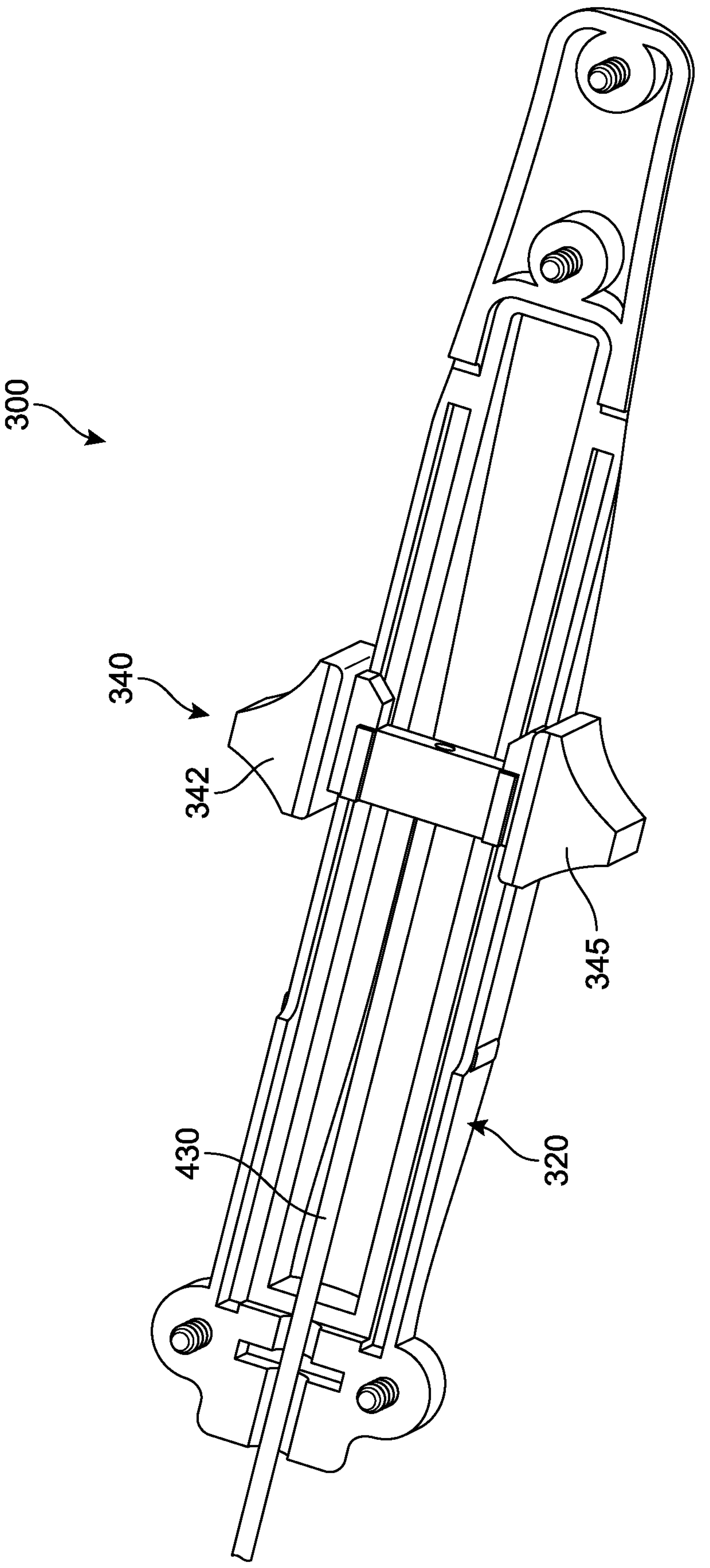
FIG. 18 is a schematic view of the handle of the implant delivery device with an outer panel removed to reveal the inner components of the handle.

FIG. 18 is a schematic view of the handle of the implant delivery device with an outer panel removed to reveal the inner components of the handle. FIG. 18 is included to further illustrate the details of slider member 340 and the attached inner shaft 430.

Figure 19:
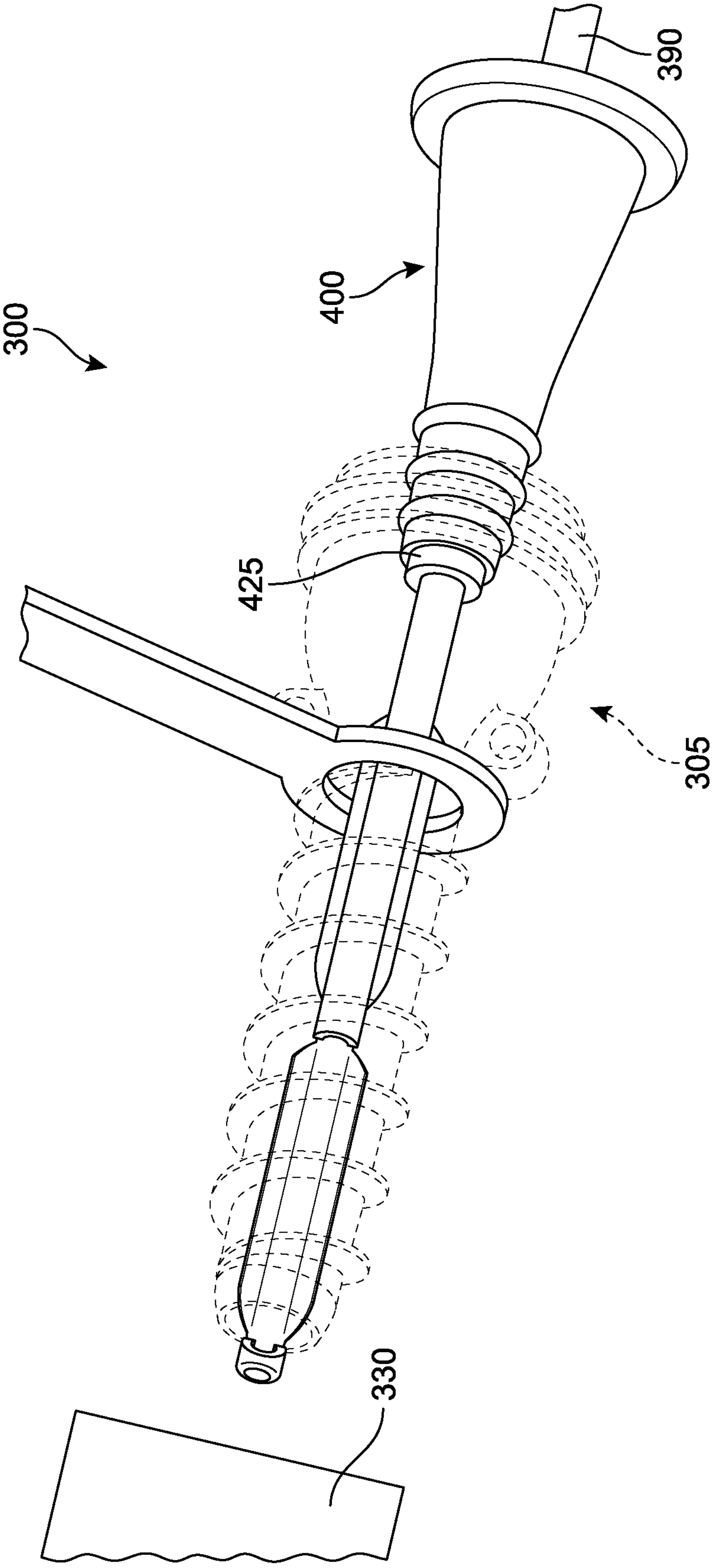
FIG. 19 is a schematic view of the implant delivery device being withdrawn through the cannula with the cannula shown in phantom to reveal the ring on the outer shaft of the implant delivery device pulling the cannula seal member out of the cannula.

FIG. 19 is a schematic view of the implant delivery device being withdrawn through the cannula with the cannula shown in phantom to reveal the ring on the outer shaft of the implant delivery device pulling the cannula seal member out of the cannula. As shown in FIG. 19, ring 425 on outer shaft 390 is abutted against the distal end of cannula sealing member 400. Accordingly, because of the positioning of ring 425, withdrawal of outer shaft 390 through cannula 305 unseats cannula sealing member 400 from cannula, permitting full removal of implant delivery device 300 without cannula sealing member 400 remaining stuck within cannula 305 and sliding off the end of outer shaft 390.

Figure 20:
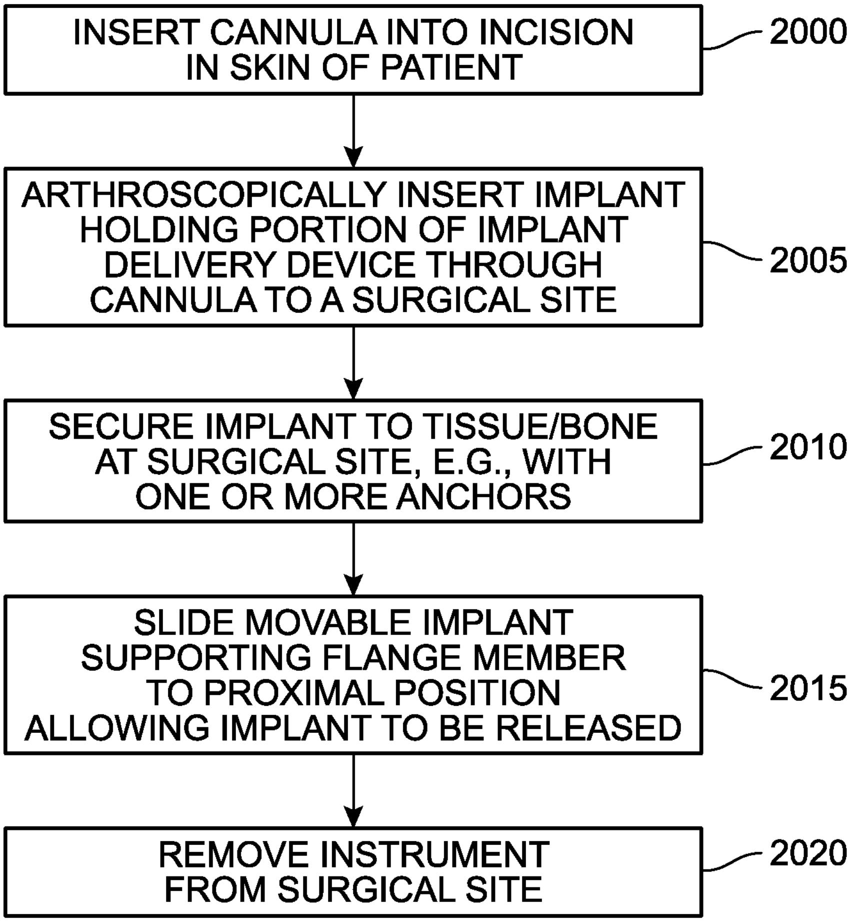
FIG. 20 is a flowchart illustrating a method of delivering a sheet-like implant to a surgical site using the implant delivery device shown and discussed with respect to FIGS. 3-19.

FIG. 20 is a flowchart illustrating a method of delivering a sheet-like implant to a surgical site using the implant delivery device shown and discussed with respect to FIGS. 3-19. As shown in FIG. 20, the method of delivering the implant may include inserting a cannula into an incision in the skin of a patient. (Step 2000.) In some embodiments, the method may include placing a sheet-like implant into the implant holding portion of the implant delivery device. However, in other embodiments, this process of loading the implant into the implant delivery device may be done as a manufacturing step, and the loaded implant delivery device may be provided to the surgeon ready for use.

In addition, once the cannula is inserted, the method may also include arthroscopically inserting the implant holding portion of the implant delivery device through the cannula to a surgical site. (Step 2005.) It will be noted that, in some cases, the implant delivery device may be used in non-arthroscopic (e.g., open) surgeries. It will be further noted that the disclosed implant delivery device need not necessarily be used with a cannula such as cannula 305. If the implant delivery device were to be used during an open surgery, the cannula would not be necessary.

The next step in the method involves the securing of the implant to tissue/bone at the surgical site, for example, with one or more anchors. (Step 2010.) Once the implant has been secured, the movable implant supporting flange member may be moved to the proximal position (by moving the slider member in the proximal direction) allowing the implant to be released. (Step 2015.) Finally, once the implant has been released, the instrument (i.e., the implant delivery device) may be removed from the surgical site. (Step 2020.)

In some embodiments, one or both of the implant supporting flange members may have a different configuration in order to maximize utility in delivering the sheetlike implant to the surgical site and hold the implant in place while anchors are inserted therein.

Figure 21:
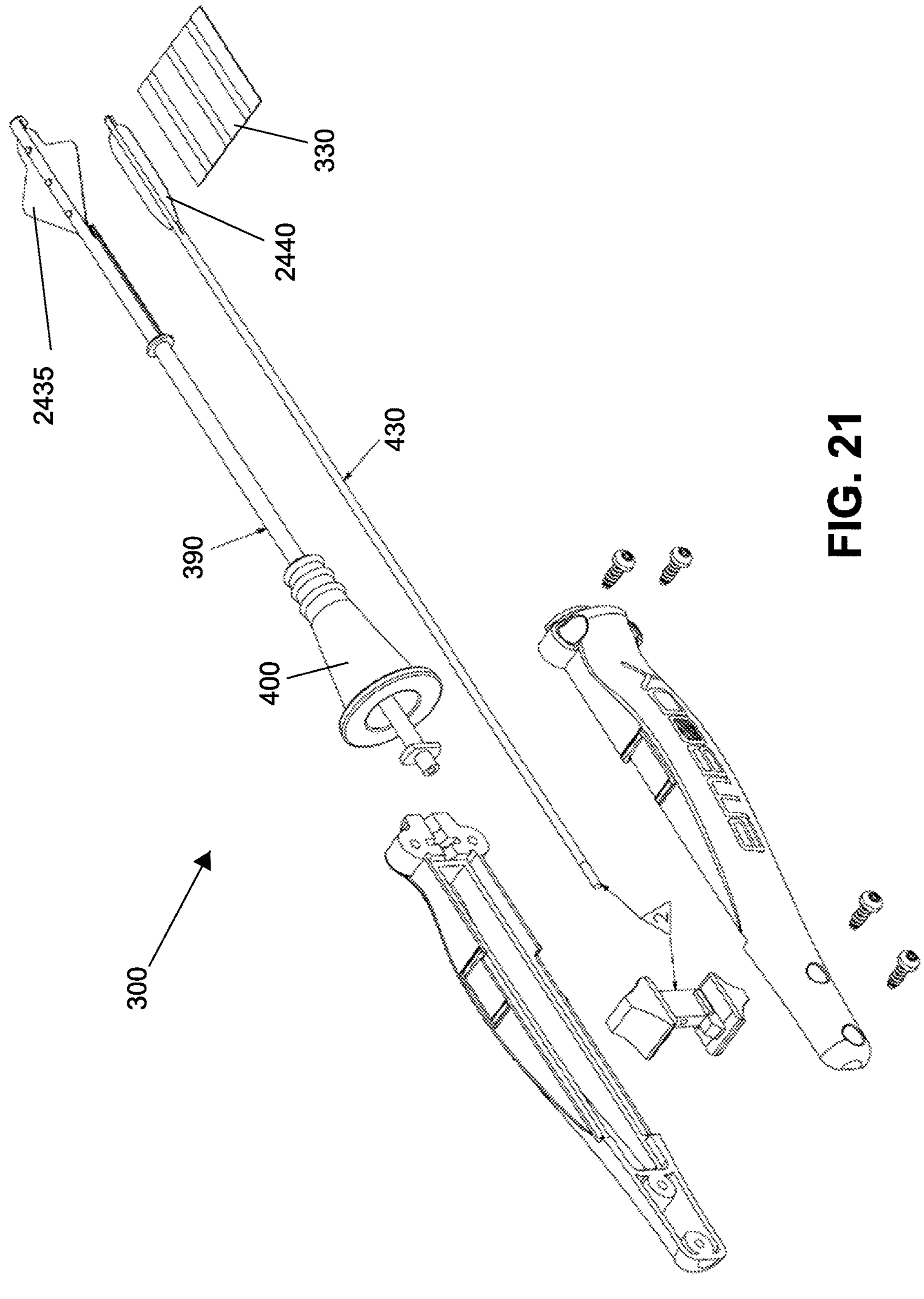
FIG. 21 is a schematic exploded view of an implant delivery device including a fixed implant supporting flange member having wings.

FIG. 21 is a schematic exploded view of an implant delivery device including a fixed implant supporting flange member having wings. As shown in FIG. 21, substantially the same implant delivery device may be used with a differently shaped fixed implant supporting flange member 2435. In this case, fixed implant supporting flange member 2435 may include a pair of substantially triangular shaped wings extending from a centerline axis of outer shaft 390 of device 300. A narrow movable implant supporting flange member 2440, similar to movable implant supporting flange member 440 may be used with fixed implant supporting flange member 2440.

Figure 22:
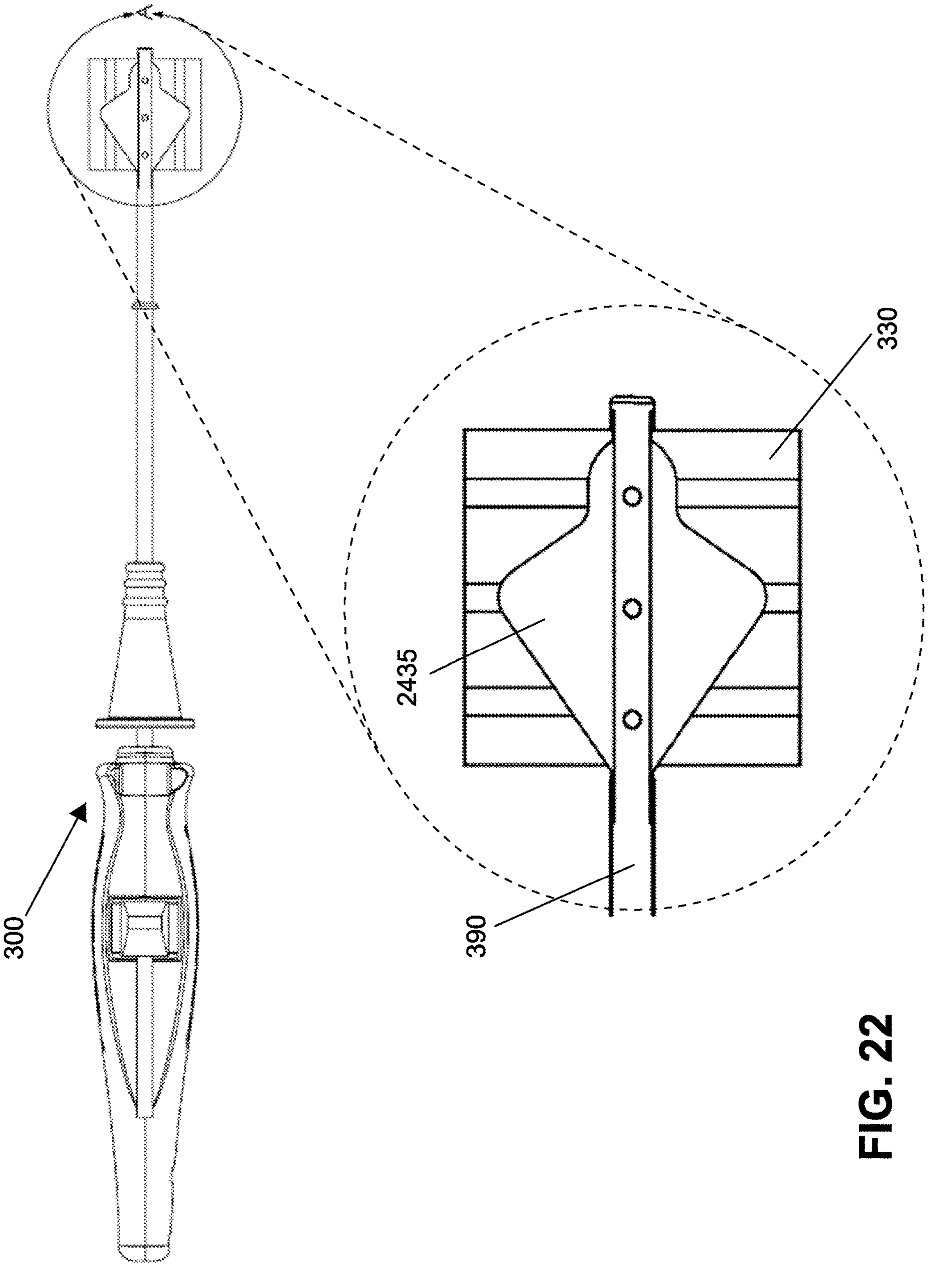
FIG. 22 is a schematic superior view of an implant delivery device with an enlarged view of an implant holding portion holding an implant using a fixed implant supporting flange member having wings.

FIG. 22 is a schematic superior view of an implant delivery device with an enlarged view of an implant holding portion holding an implant using fixed implant supporting flange member 2435 having wings. As shown in FIG. 22, flange member 2435 has a surface area that fits within the confines of implant 330.

Figure 23:
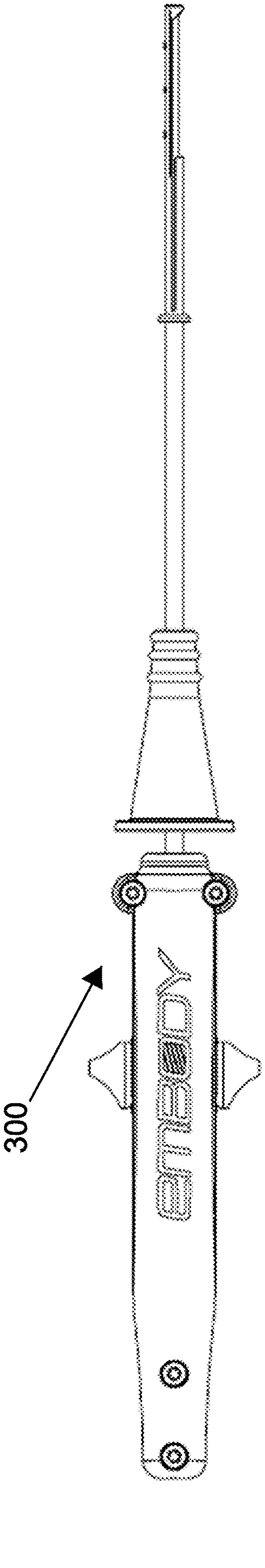
FIG. 23 is a schematic side view of an implant delivery device.

FIG. 23 is a schematic side view of implant delivery device 300

Figure 24:
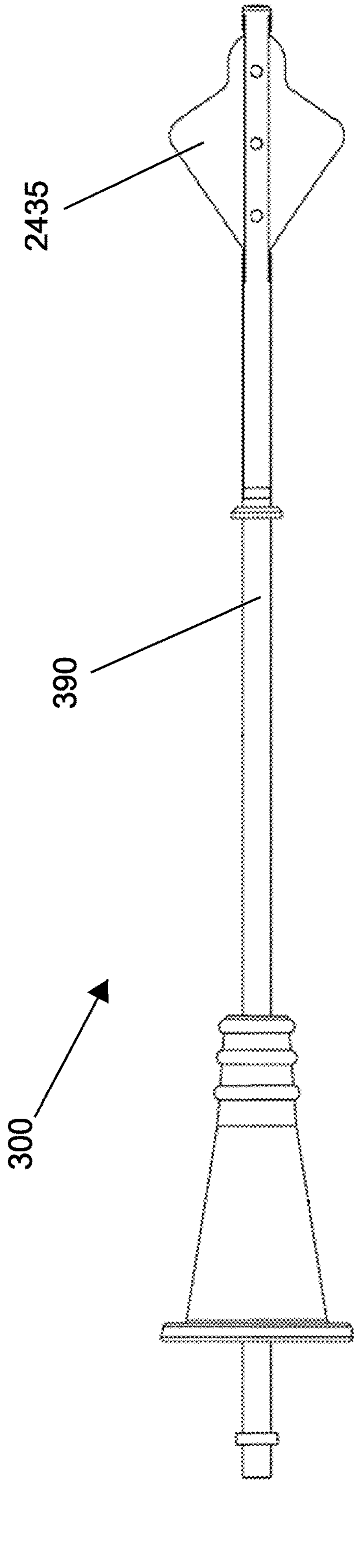
FIG. 24 is a schematic superior view of a portion of the implant delivery device including the implant holding portion having a fixed implant supporting flange member with wings.

FIG. 24 is a schematic superior view of a portion of the implant delivery device including the implant holding portion having a fixed implant supporting flange member with wings, but without an implant loaded into the implant holding portion.

Figure 25:
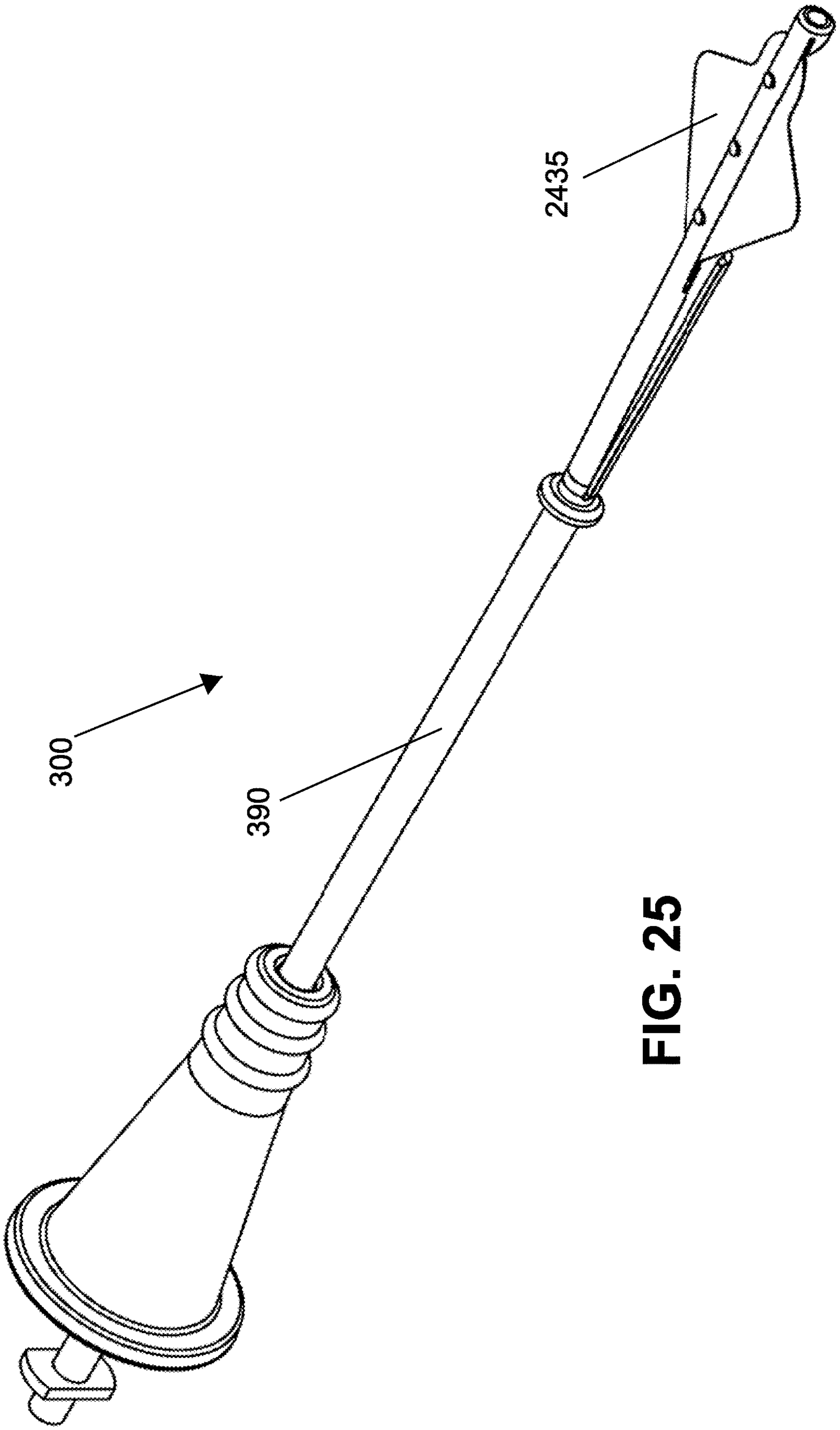
FIG. 25 is a schematic superior perspective view of the implant delivery device including the implant holding portion having a fixed implant supporting flange member with wings.

FIG. 25 is a schematic superior perspective view of the implant delivery device including the implant holding portion having a fixed implant supporting flange member with wings, but without an implant loaded into the implant holding portion.

Figure 26:
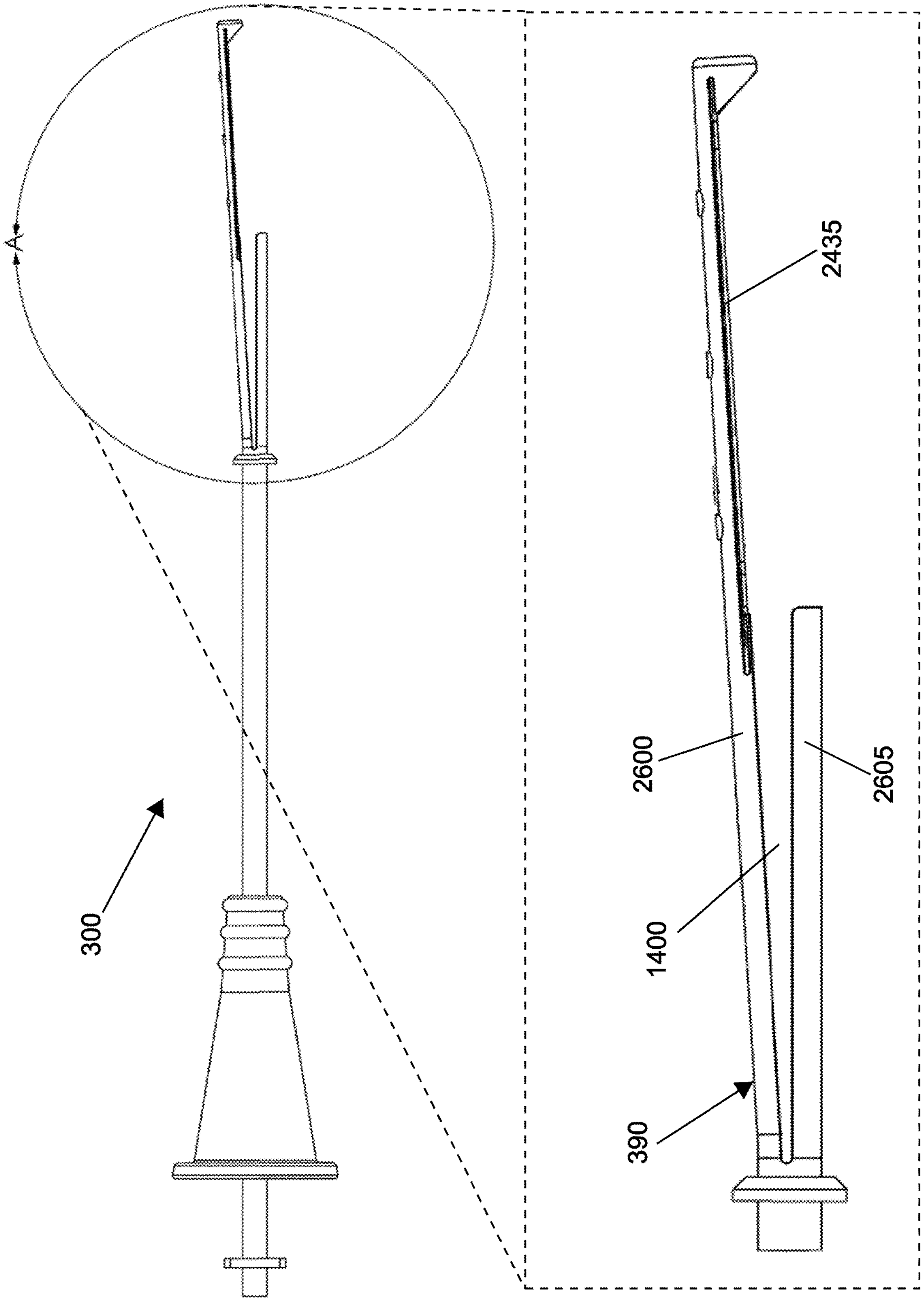
FIG. 26 is a schematic side view of an implant delivery device illustrating a slot between portions of the implant holding portion of the device.

FIG. 26 is a schematic side view of an implant delivery device illustrating slot 1400 between portions of the implant holding portion of the device. Slot 1400 is discussed in greater detail above with respect to FIG. 14.

Figure 27:
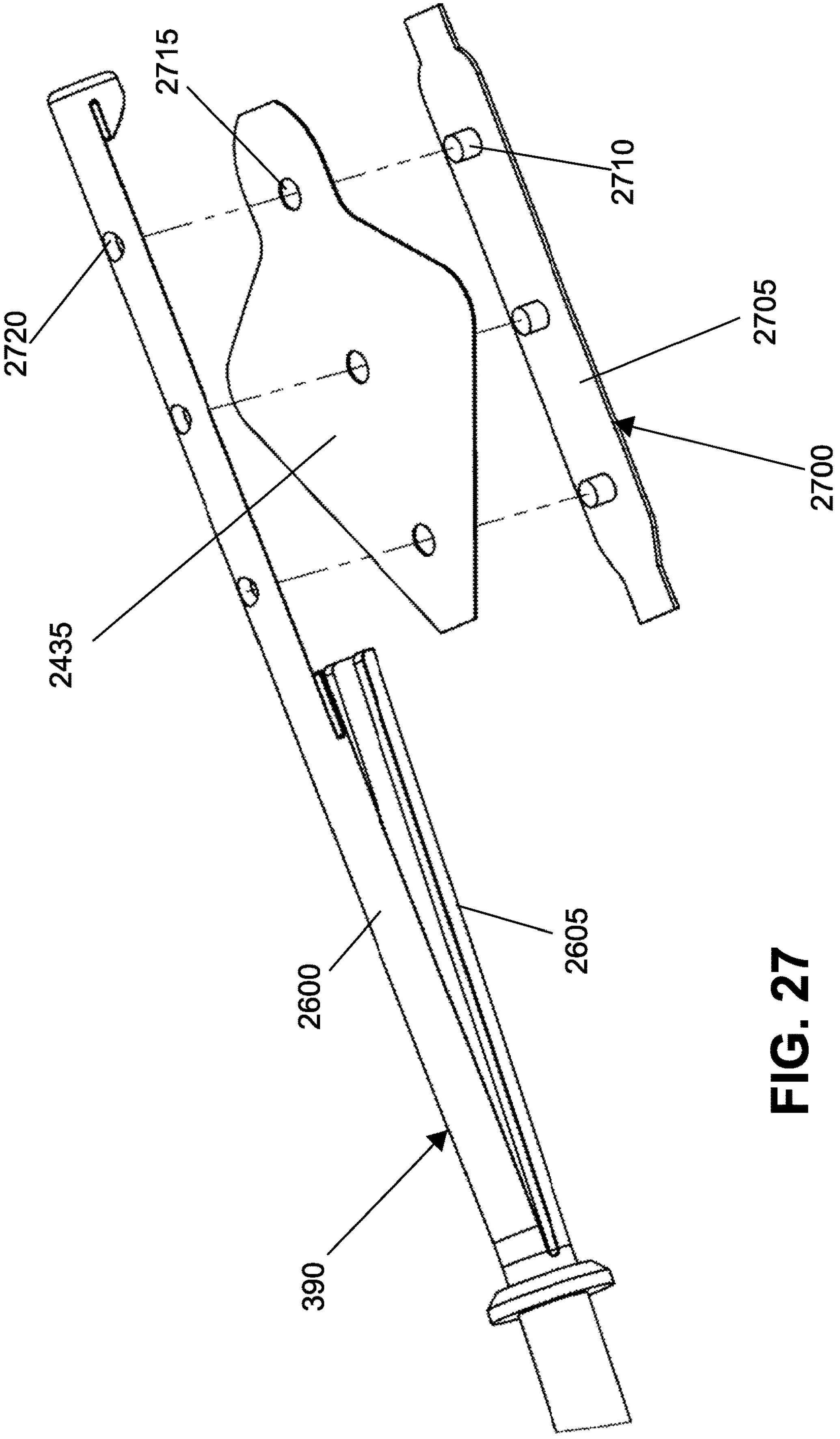
FIG. 27 is a schematic perspective exploded view of an implant delivery device showing a rivet strip that attaches the fixed implant supporting flange member to the outer shaft of the device.

FIG. 27 is a schematic perspective exploded view of an implant delivery device showing a rivet strip that attaches the fixed implant supporting flange member to the outer shaft of the device. In some embodiments, fixed implant supporting flange member 2435 may include one or more holes 2715 for receiving a rivet of a rivet strip 2700 to secure fixed implant supporting flange member 2435 to outer shaft 390 of the device.

As shown in FIG. 27, rivet strip 2700 may include a base portion 2705 from which a plurality of cylindrical projections 2710 may extend. During assembly, the cylindrical projections 2710 are inserted through holes 2715 in flange member 2435 and then through holes 2720 in outer shaft 390. Cylindrical projections 2710 are then crushed to enlarge the projection and prevent it from backing out of outer shaft 390, thus providing a rivet effect. (See assembled device in FIG. 25.)

Figure 28:
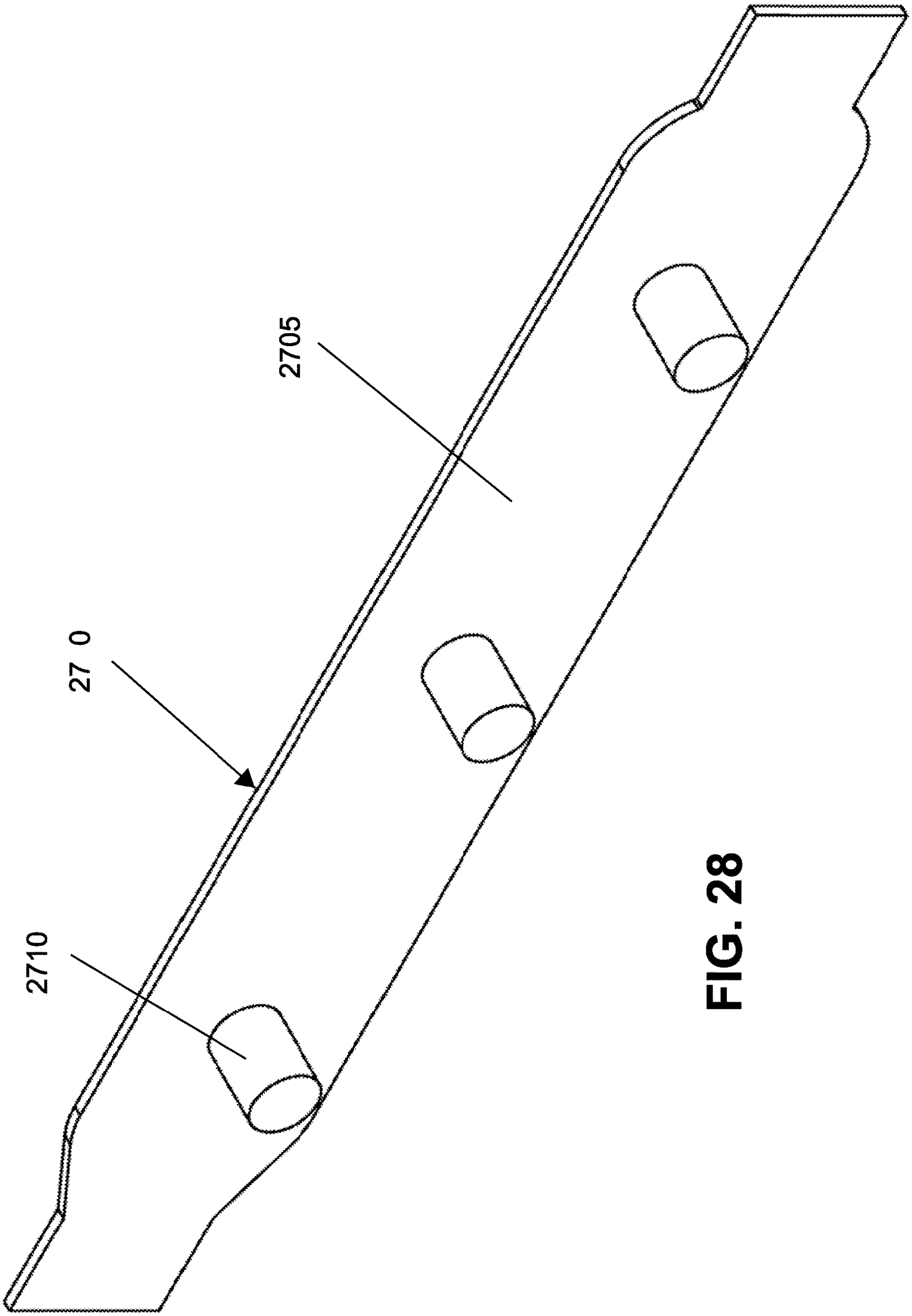
FIG. 28 is a schematic perspective view of the rivet strip.

FIG. 28 is a schematic perspective view of rivet strip 2700.

Figure 29:
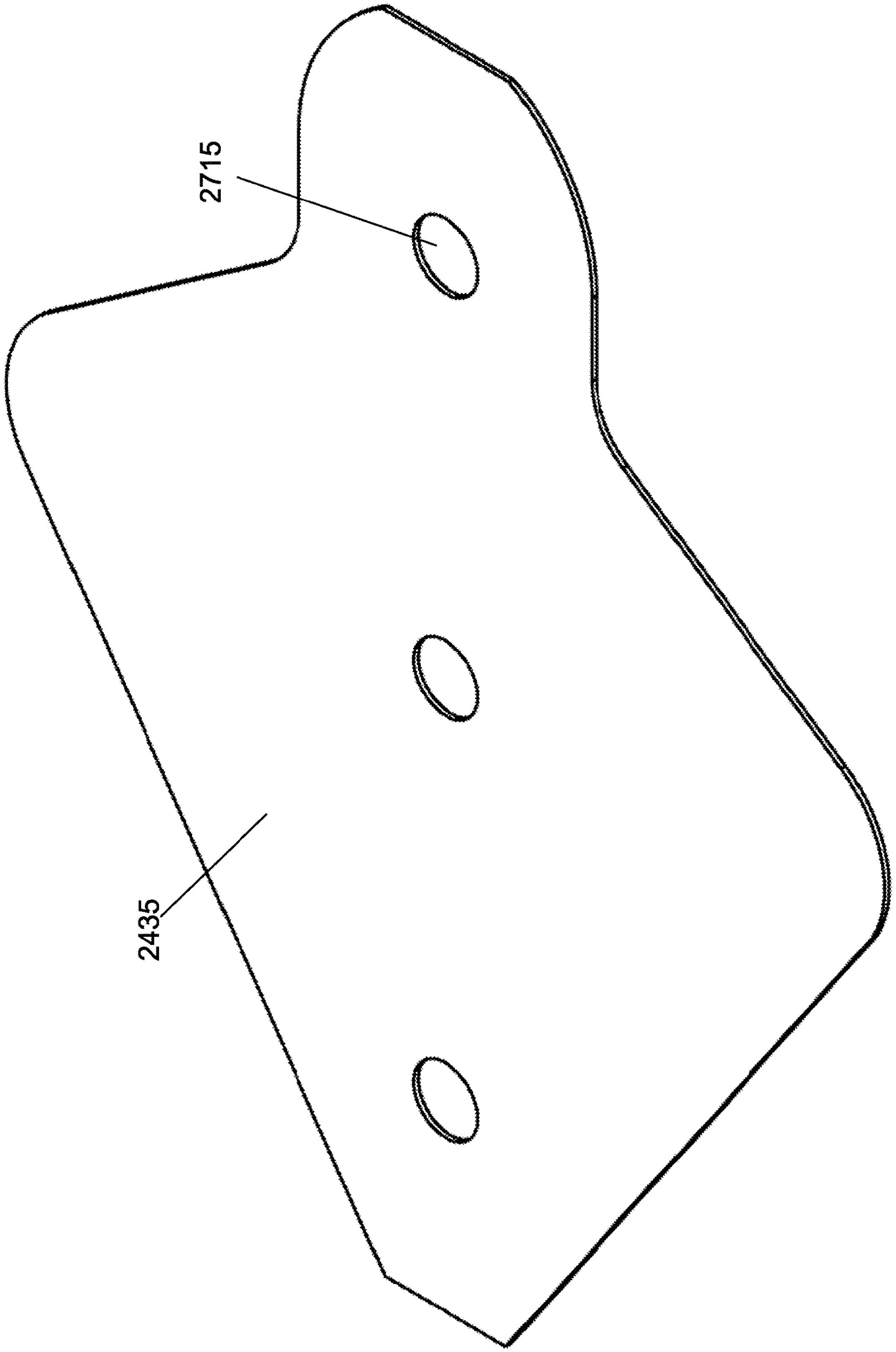
FIG. 29 is a schematic perspective view of the fixed implant supporting flange member having wings.

FIG. 29 is a schematic perspective view of fixed implant supporting flange member 2435 having wings.

Figure 30:
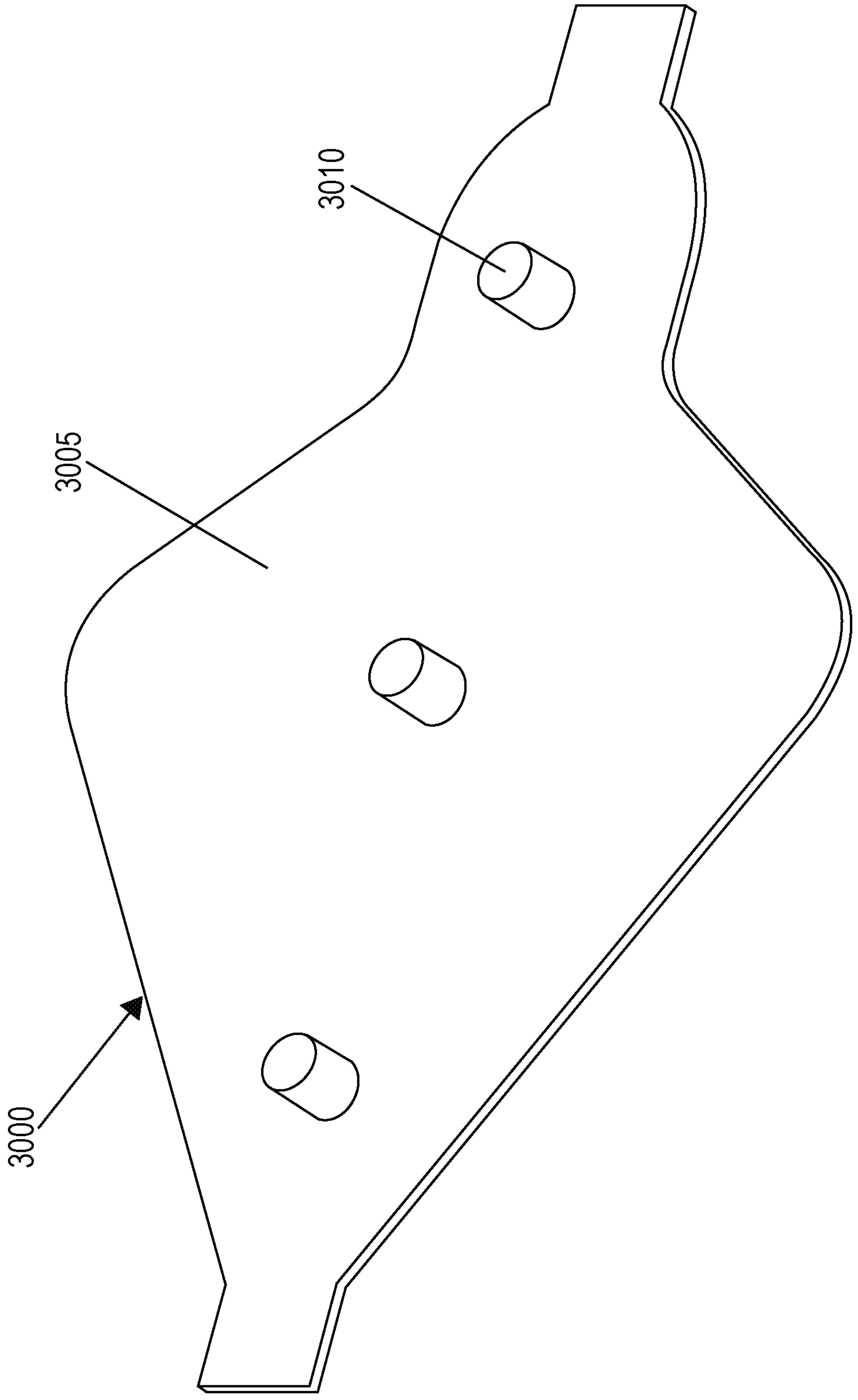
FIG. 30 is a schematic perspective view of an alternative embodiment of the fixed implant supporting flange member in which the cylindrical projections that are formed into rivets are integral with the fixed implant supporting flange member itself.

In some embodiments, the cylindrical projections may be integrated into the fixed implant supporting flange member, thus eliminating the need for a separate rivet strip. FIG. 30 is a schematic perspective view of an alternative embodiment of a fixed implant supporting flange member in which the cylindrical projections that are formed into rivets are integral with the fixed implant supporting flange member itself. As shown in FIG. 30, a fixed implant supporting flange member 3000 may include a base portion 3005 from which a plurality of cylindrical projections 3010 may extend, forming a rivet configured to secure fixed implant supporting flange member 3000 to the outer shaft of the device.

Multiple designs of the flange members are disclosed herein. Most of these designs have been evaluated through testing. Among the attributes considered when designing and testing flange members are the ease of getting the introducer in and out of arthroscopic space including getting the flange/implant assembly through the cannula in both directions (i.e., ingress and egress). Also considered was the ability of the flange to control of the implant, particularly at the surgical site, through which there is a perpetual flow of fluid, which tends to displace the sheet-like implant. In addition, it was considered how much of the implant is exposed for anchoring, e.g., at the corners. The overall size and shape of the flange member relative to the sheet-like implant determine how much surface area of the implant is exposed for anchoring.

Figure 31:
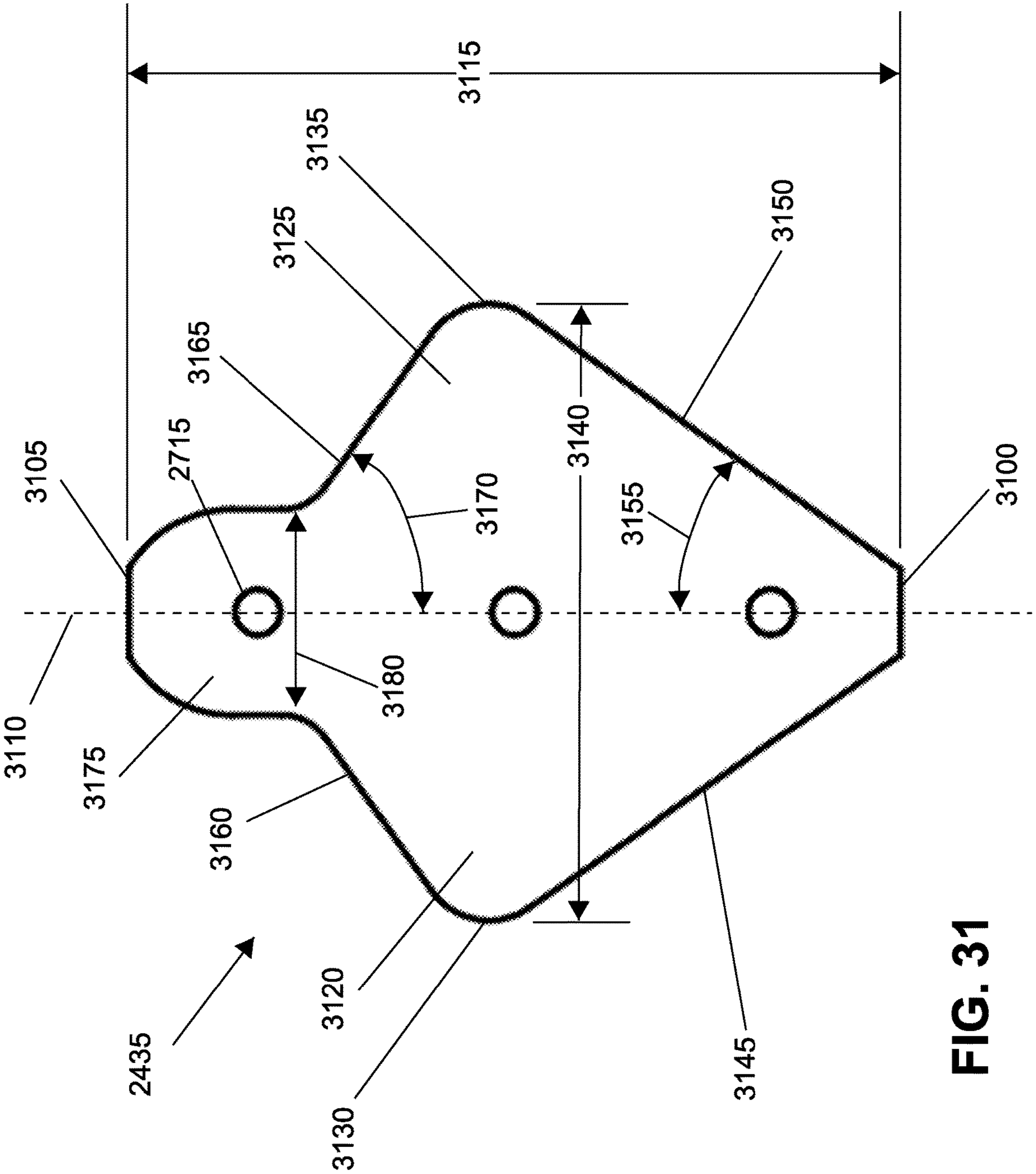
FIG. 31 is a schematic view of a fixed implant supporting flange member having wings.

FIG. 31 is a schematic view of a fixed implant supporting flange member having wings. Although a multitude of possible flange member designs are discussed below, the shape shown in FIG. 31 tested particularly well. The features of this design will now be discussed below in detail.

Most notably, the embodiment shown in FIG. 31 includes a pair of wings extending from a centerline axis of the outer shaft. These wings are substantially flexible in order to enable the flange member to collapse when being inserted through the cannula, but resilient so that it lays open the implant upon exiting the cannula into the surgical space. In some embodiments, such wings may have a substantially triangular shape, as shown in FIG. 31. Flange member 2435 may have a proximal end 3100 and a distal end 3105. (It will be noted that, in FIGS. 31-94, all flange members are illustrated in the same orientation, i.e., with the proximal end toward the bottom of the page and the distal end toward the top of the page.)

Flange members having different thicknesses were tested. In particular, thinner flange members having a thickness of 0.005 inches were tested, as well as thicker flange members having a thickness of 0.01 inches. Across most designs, including that shown in FIG. 31, a thinner die cut UHMWPE film, having a thickness of 0.005" performed better. While thicker (0.01") flange members provided better control of the implant, they were more difficult to pass through the cannula. Instead of the stiffer (i.e., thicker) flange member, the implant was stiffened, reducing the need for stiffness from the flange member. In some embodiments, an injection-molded LDPE flange member may be used to increase stiffness without reducing performance on ingress and egress.

In FIG. 31, a centerline axis 3110 is shown, which represents the centerline axis of flange member 2435 and, when the flange member is assembled with the insertion device, also represents the centerline axis of outer shaft 390 of device 300. In some embodiments, flange member 2435 may be symmetrical across centerline axis 3110, as shown in FIG. 31. As further shown in FIG. 31, flange member 2435 may have an overall length 3115 extending from proximal end 3100 to distal end 3105.

As also shown in FIG. 31, fixed implant supporting flange member 2435 may include a first wing 3120 and a second wing 3125. First wing 3120 may extend to a first wing tip 3130. Second wing 3125 may extend to a second wing tip 3135. As shown in FIG. 31, fixed implant supporting flange member 2435 may have a maximum width 3140 extending from first wing tip 3130 of first wing 3120 to second wing tip 3135 of second wing 3125. During testing with a 30 mm wide implant, the design shown in FIG. 31 tested best with a maximum tip-to-tip width 3140 of 24 mm.

It will be noted that all fixed implant supporting flange member designs discussed herein were tested with an 8 mm wide movable implant supporting flange member and a 5.5 mm wide rivet strip.

As shown in FIG. 31, in some embodiments, fixed implant supporting flange member 2435 may include a necked down portion 3175 at distal end 3105, wherein necked down portion 3175 has a narrower width than maximum width 3140 of the wings. Accordingly, fixed implant supporting flange member 2435 may be asymmetrical in the proximal-distal direction. Necked down portion 3175 provides additional area at the distal corners of the implant for insertion of anchors. The distal corners of the implant tend to be pushed/swept back during insertion of the assembly. Therefore, it is beneficial to provided added clearance to expose more of the implant at the distal corners. (See area 3210 in FIG. 32.)

As shown in FIG. 31, first wing 3120 may have a first proximal edge 3145 that extends at a first angle with respect to centerline axis 3110. Similarly, second wing 3125 may have a second proximal edge 3150 that extends a second angle 3155 with respect to centerline axis 3110. These angles of the proximal edges are preferred to be shallower in order to facilitate egress through the cannula.

In addition, as shown in FIG. 31, first wing 3120 may have a first distal edge 3160 that extends at a third angle from centerline axis 3110. Second wing 3125 may have a second distal edge 3165 that extends at a fourth angle 3170 from centerline axis 3110. These distal angles are preferred to be larger in order to expose more of the implant at the distal corners. Accordingly, the distal angles of the distal wing edges may be larger than the proximal angles of the proximal wing edges.

It will also be noted that gently curved wing edge transitions may be used to better prevent damage to the implant. For example, as shown in FIG. 31, first wing tip 3130 of first wing 3120 and second wing tip 3135 of second wing 3125 may be substantially curved.

Figure 32:
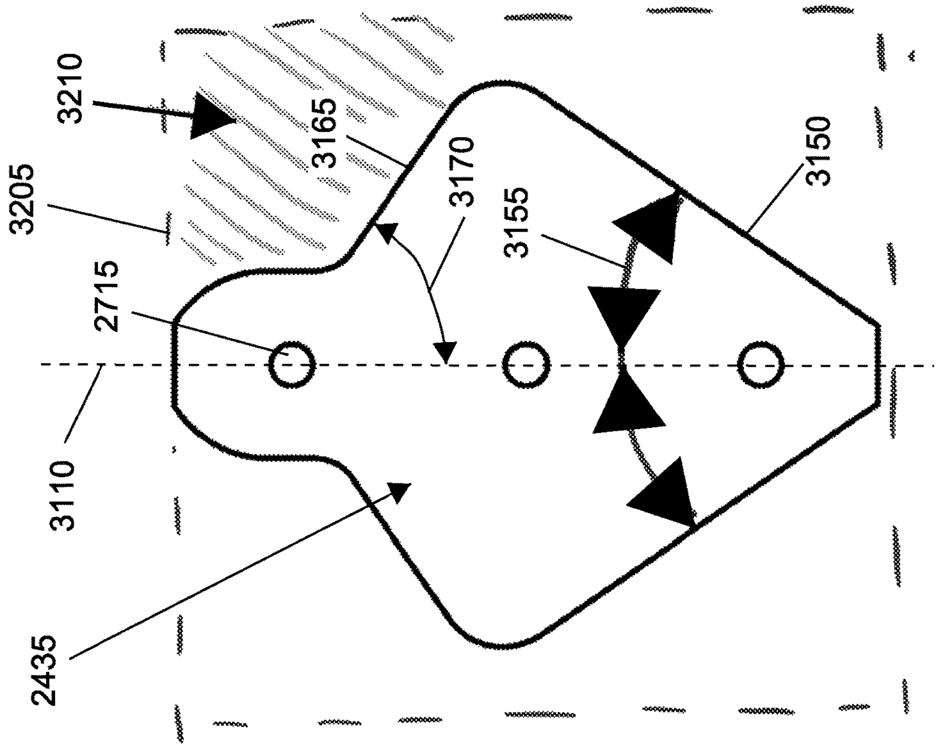
FIG. 32 is a schematic view illustrating the size relationship between the fixed implant supporting flange member and an implant.
Figure 38:
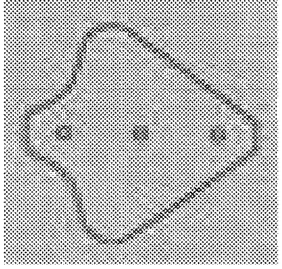

It will be noted that in some embodiments, the edges of the wings may be substantially linear as shown in FIG. 32. In some embodiments, the edges of the wings may be curved. For example, as shown in FIG. 38, some edges of the wings may be concave. The linear/curved design of the wing edges may affect not only the ease with which the flange members may be inserted and/or withdrawn through the cannula, but also how the flange members hold the implant.

It will also be noted that it may work better with some designs to roll the implant in the superior direction (i.e., back toward the fixed implant supporting flange member), instead of in the inferior direction, prior to feeding the assembly through the cannula during insertion.

FIG. 32 is a schematic view illustrating the size relationship between the fixed implant supporting flange member and an implant. As shown in FIG. 32, a dashed outline shows an exemplary implant 3205 with respect to flange member 2435. FIG. 32 illustrates how the large wing edge angle 3170 provides an enlarged exposed distal corner region 3210 of implant 3205. This enlarged area of implant 3205 is available for inserting one or more anchors.

Figure 33:
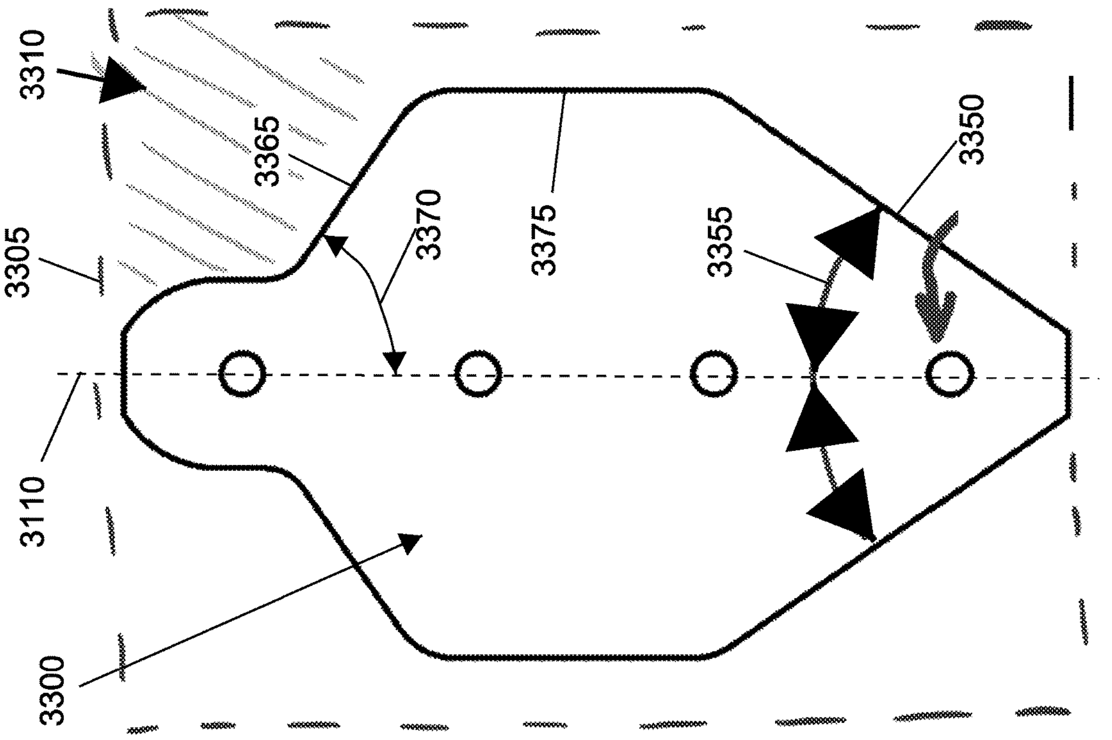
FIG. 33 is a schematic view illustrating the size relationship between a longer fixed implant supporting flange member with wings and a longer implant.

It will be noted that FIG. 32 illustrates use of flange member 2435 with a square implant shape, e.g., 30 mm×30 mm. In some embodiments, an elongated flange member may be used with an elongated implant, e.g., 30 mm×40 mm. FIG. 33 is a schematic view illustrating the size relationship between a longer fixed implant supporting flange member with wings and a longer implant. It will be noted that the elongated flange member 3300 shown in FIG. 33 maintains the same proximal wing edge angle 3355 as corresponding angle 3155 in flange member 2435. Similarly, elongated flange member 3300 maintains the same distal wing edge angle 3370 as corresponding angle 3170 in flange member 2435. Again, these angles facilitate ingress and egress through the cannula. In order to provide the added length of flange member 3300, the wing tips may form elongated edges 3375. In some embodiments, elongated edges 3375 may extend in a longitudinal direction in substantial alignment with centerline axis 3110.

Figure 34:
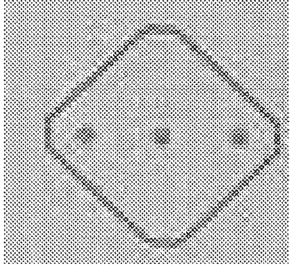
FIGS. 34-89 are schematic views of alternative embodiments of fixed implant supporting flange members.
Figure 89:
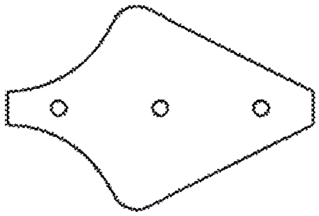
Figure 88:
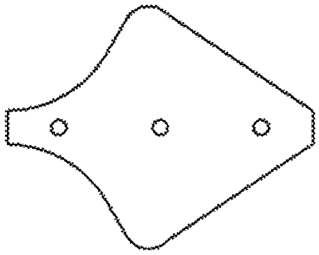
Figure 87:
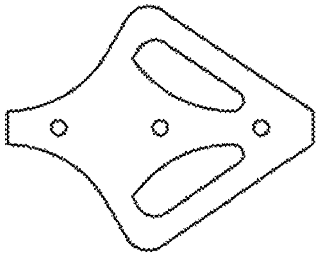
Figure 86:
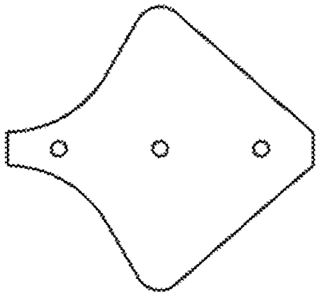
Figure 85:
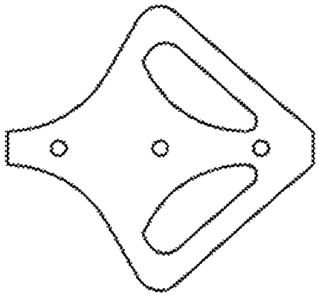

FIGS. 34-89 are schematic views of alternative embodiments of fixed implant supporting flange members. It will be noted that the flange member configurations are designed according to competing interests. For example, wider flanges are generally better at controlling the implant, particularly in the surgical environment with the flow of saline at the surgical space, but leave less room for anchors and are more difficult on ingress and egress through the cannula. Narrower flanges pass through the cannula well, but do not control the implant as well, although they do provide larger spaces for anchoring on the implant because they cover less surface area of the implant. Windows add flexibility to the wings and control the implant well. One noteworthy consideration is the possibility of making the wings too flexible if the windows are too large relative to the overall surface area of the wings.

In some embodiments, flange members may be symmetrical about the centerline axis. In other embodiments (not shown), flange members may be asymmetrical about the centerline axis. In addition, as discussed above, flange members may be asymmetrical in the proximal-distal direction. In some embodiments, however, flange members may be symmetrical or substantially symmetrical in the proximal-distal direction (i.e., longitudinally), as shown in FIGS. 34-37. Longitudinally symmetrical flange members tend to perform well on both ingress and egress.

In some embodiments, the wings of the implant may include one or more windows. Such windows perform several functions. First, windows represent a removal of material from the wing, thus making the wing more flexible. Second, windows may provide increased hold of the sheet-like implant, which may protrude partially through the windows when loaded into the device. Third, windows expose additional portions of the implant for insertion of anchors.

Figure 35:
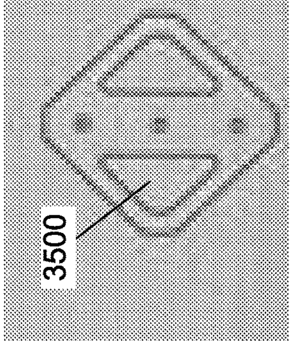

FIG. 35 shows a flange member having windows 3500. Other flange members with windows are shown in FIGS. 39, 45, 46, 49, 51, 58, 59, 62, 63, 66, 67, 70, 71, 73, 7 4, 77, 79, 85, and 87. The performance characteristics of flange members having windows may be determined by various factors, including the size, shape, and placement of the windows.

Figure 36:
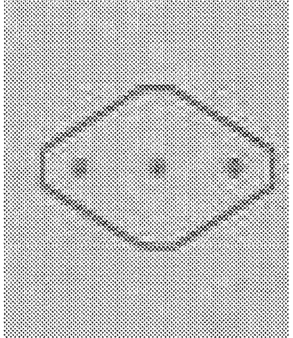
Figure 37:
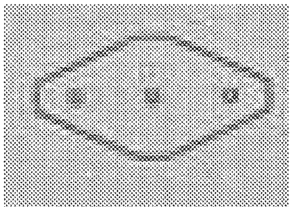

During testing, a 20 mm wide, 0.01" thick version of the embodiment shown in FIG. 36 provided excellent control of the implant and performed well during ingress and especially egress through the cannula.

During testing, a 28 mm wide, 0.01" thick version of the embodiment shown in FIG. 38, performed well in terms of laying the implant very nicely in space at the surgical site.

Figure 39:
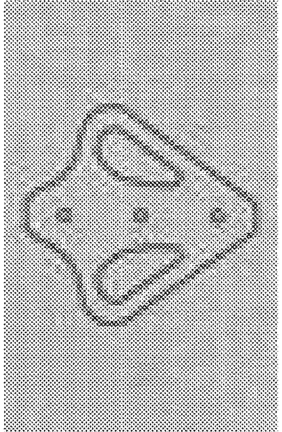

During testing, a 28 mm wide, 0.01" thick version of the embodiment shown in FIG. 39 performed excellent at holding the implant. A thinner version (0.005") performed better on egress, but the thicker version performed better at controlling the posterior portion of the implant, leading to an overall better performance by the thicker version.

Figure 40:
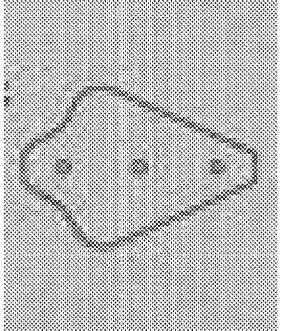

During testing, a 20 mm wide, 0.01" thick version of the embodiment shown in FIG. 40 performed well on ingress and egress, and "rocking" the instrument worked well to flatten the implant after ingress through the cannula.

Figure 41:
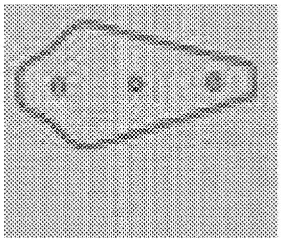

A 15 mm wide, 0.01" thick version of the embodiment shown in FIG. 41 performed well on ingress and egress, as expected of a narrower design, and held the implant better than the standard 8 mm wide substantially octagonal design shown in FIGS. 13-16.

Figure 42:
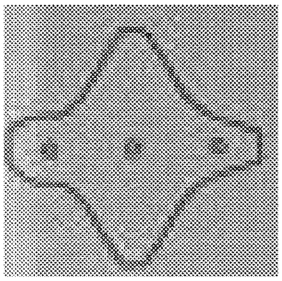

A 28 mm wide, 0.005" thick version of the embodiment shown in FIG. 42 performed even better in terms of implant control than the implants having the shape shown in FIG. 40.

Figure 43:
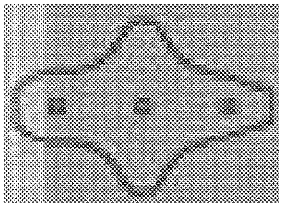
Figure 44:
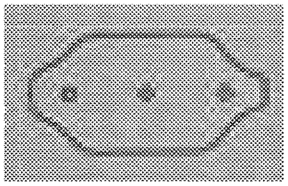
Figure 45:
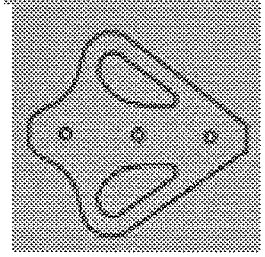
Figure 46:
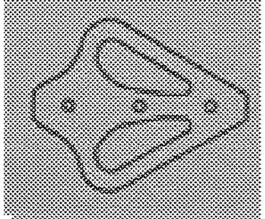
Figure 47:
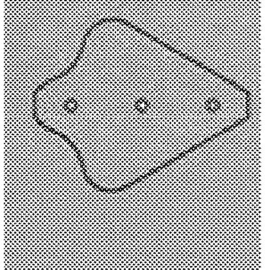
Figure 48:
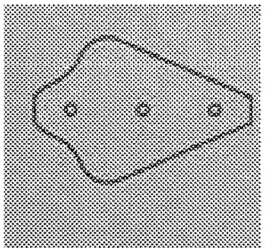
Figure 49:
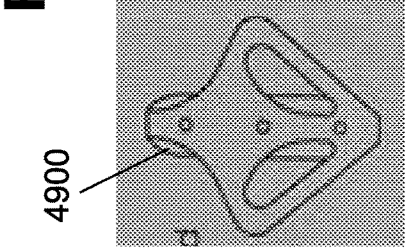
Figure 50:
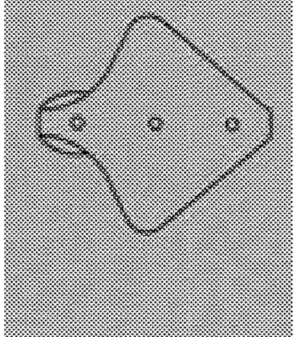
Figure 51:
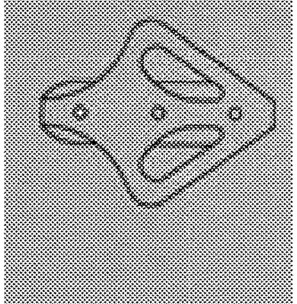

A 20 mm wide, 0.01" thick version of the embodiment shown in FIG. 43 also controlled the implant well.

Figure 52:
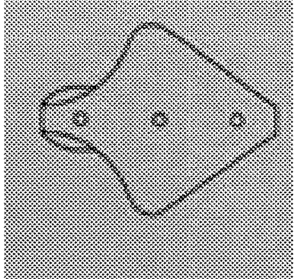
Figure 53:
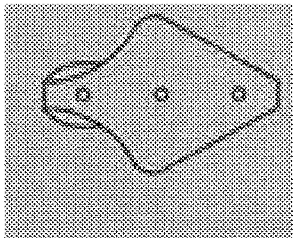
Figure 54:
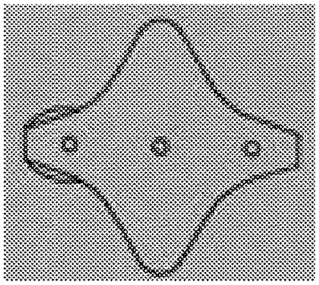
Figure 55:
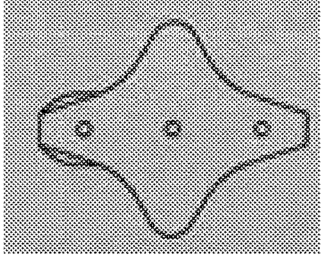
Figure 56:
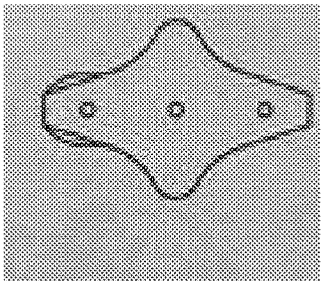
Figure 57:
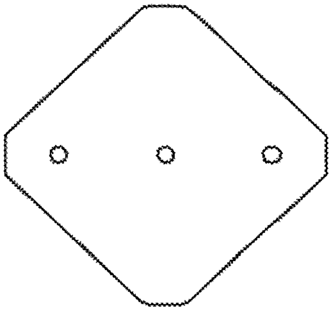
Figure 58:
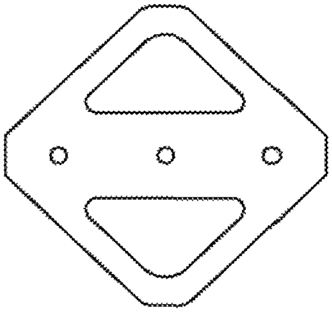
Figure 59:
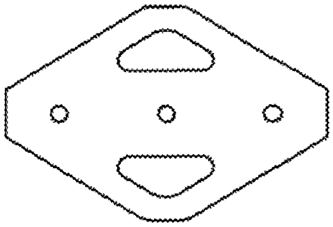
Figure 60:
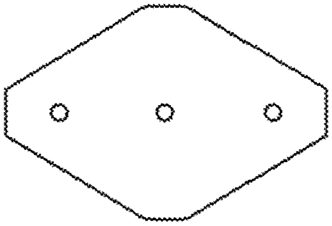
Figure 61:
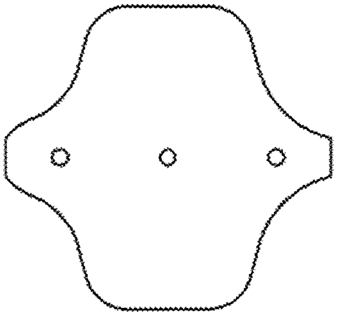
Figure 62:
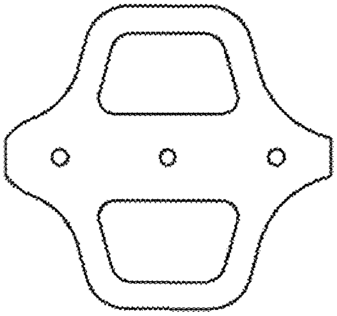
Figure 63:
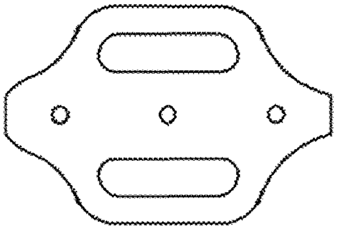
Figure 64:
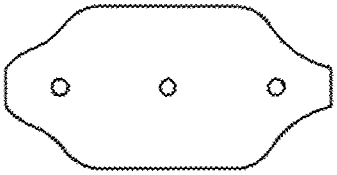
Figure 65:
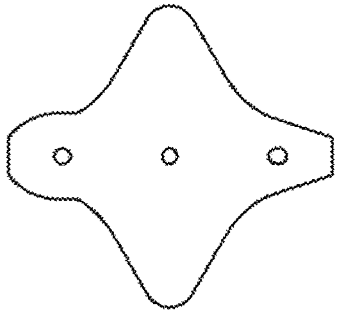
Figure 66:
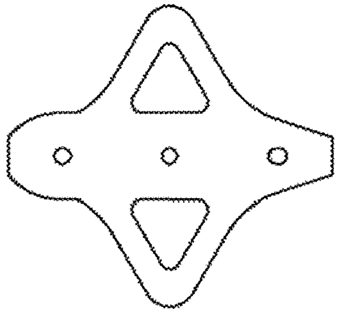
Figure 67:
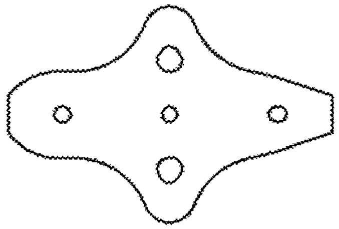
Figure 68:
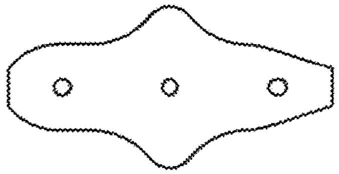
Figure 69:
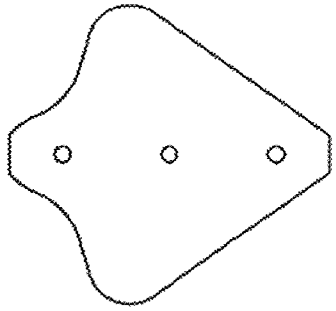
Figure 70:
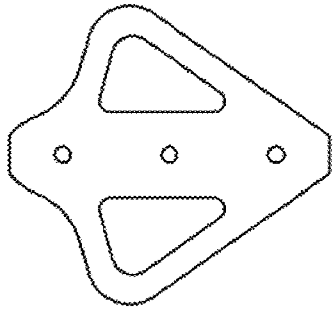
Figure 71:
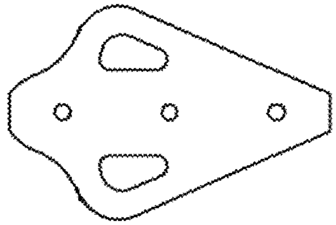
Figure 72:
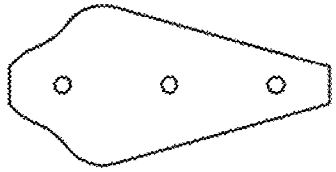
Figure 73:
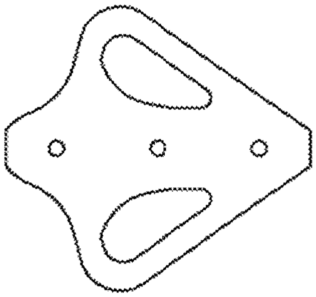
Figure 74:
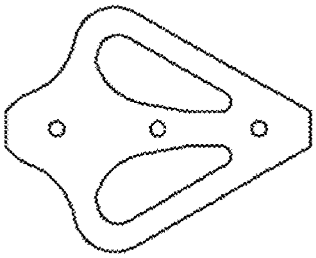
Figure 75:
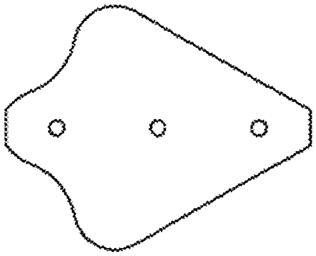
Figure 76:
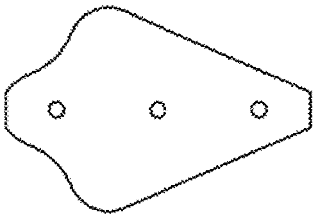
Figure 77:
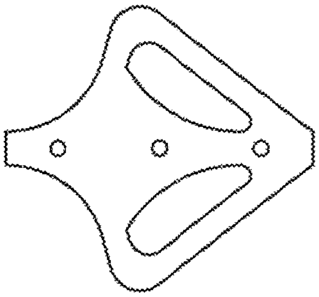
Figure 78:
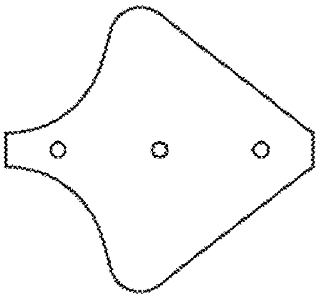
Figure 79:
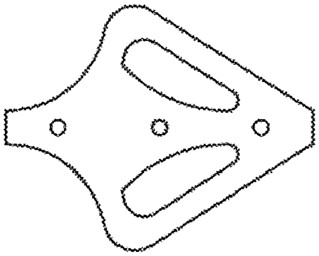
Figure 80:
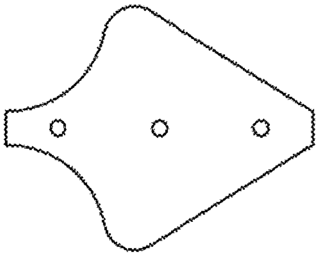
Figure 81:
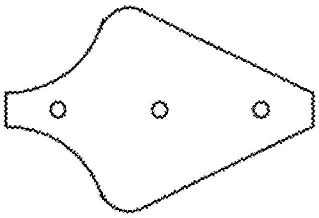
Figure 84:
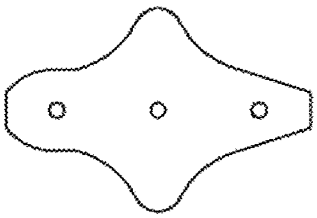
Figure 83:
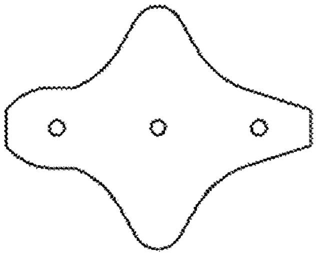
Figure 82:
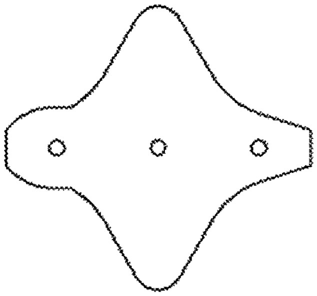

A 24 mm wide sheet version of the embodiment shown in FIG. 52, which is similar to preferred embodiment of FIG. 31, performed well as expected. It provided good balance of ingress and egress, implant control (unfolded well), and exposed ample surface area of the implant through which anchors may be inserted. The version of FIG. 52 design formed from a sheet material performed better than the same shape formed by a molding process.

In order to avoid inserting an anchor through the movable implant supporting flange member, which is hidden beneath the implant during insertion, the footprint of the movable flange member should fall within the footprint of the fixed flange member. In some embodiments, the two could have the same size and shape, if they are aligned during use. In other embodiments, the footprint of the movable flange member may be smaller than that of the fixed flange member. That is, the surface area of the movable implant supporting flange member may have a surface area that falls completely within the surface area of the fixed implant supporting flange member when the two components are overlaid. Further, in some embodiments, the movable flange member may have the same or substantially the same shape as the fixed flange member. For at least the same reasons that the fixed flange member may be formed with substantially triangular wings, it may also be beneficial to form the movable flange member from substantially triangular wings.

Figure 90:
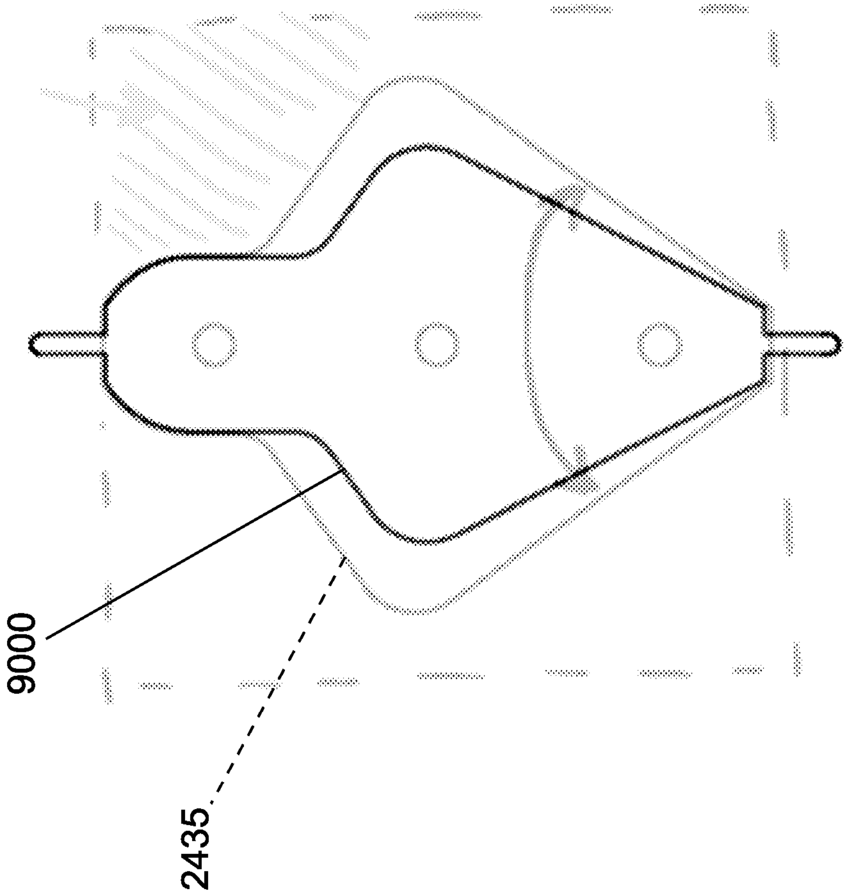
FIG. 90 is a schematic illustration of the size and shape relationship between a fixed implant supporting flange member and a movable implant supporting flange member.

FIG. 90 is a schematic illustration of the size and shape relationship between a fixed implant supporting flange member and a movable implant supporting flange member. The outline of a movable implant supporting flange member 9000 is shown overlaid fixed implant supporting flange member 2435, which is shown in phantom for contrast. As illustrated in FIG. 90, movable implant supporting flange member 900 may have a surface area that falls completely within the surface area of fixed implant supporting flange member 2435.

In the embodiment shown in FIG. 90, although shown schematically, the exemplary sizes may be an 18 mm wide movable flange member for use with a 24 mm wide fixed flange member.

Figure 91:
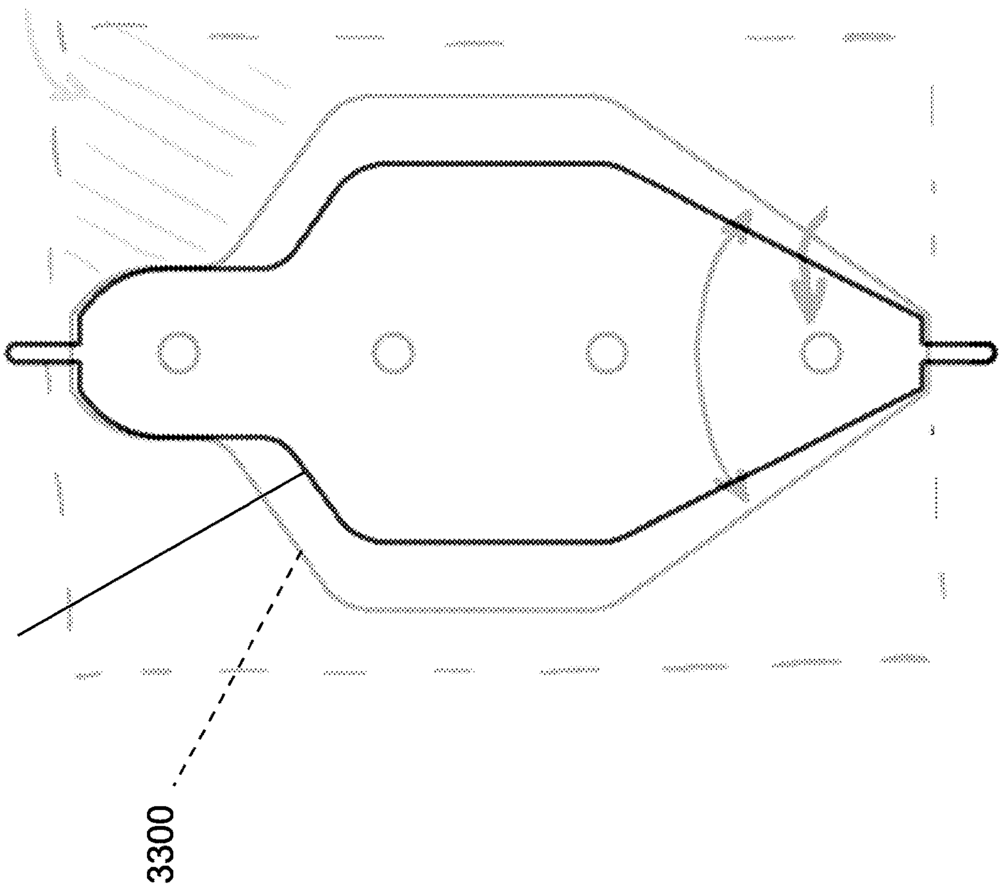
FIG. 91 is a schematic illustration of the size and shape relationship between a longer fixed implant supporting flange member and a corresponding movable implant supporting flange member.

FIG. 91 is a schematic illustration of the size and shape relationship between a longer fixed implant supporting flange member and a corresponding movable implant supporting flange member. As shown in FIG. 91, a movable implant supporting flange member 9100 may have a similar shape, but smaller surface area as fixed implant supporting flange member 3300, which is shown in phantom for comparison.

In some embodiments, one or both of the flange members may be colored. For example, in some embodiments, the fixed implant supporting flange member may be colored to facilitate visualization against the implant. This may better enable the surgeon to see which parts of the implant are available for anchoring without tacking the flange member in the process.

Figure 92:
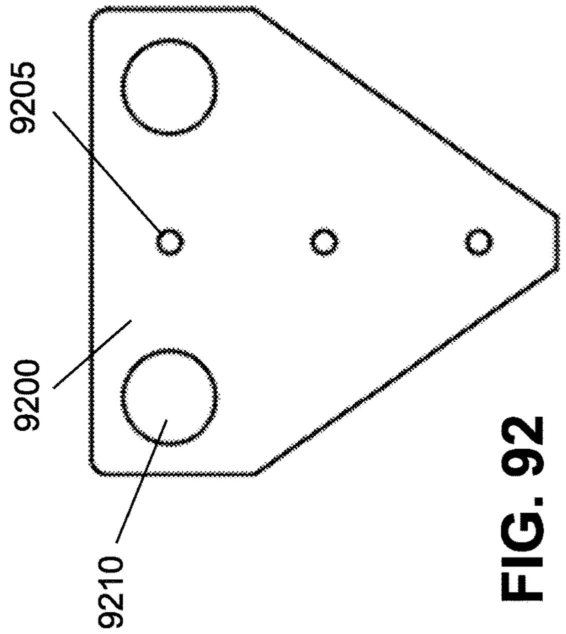
FIG. 92 is a schematic illustration of an alternative embodiment of a fixed implant supporting flange member.

FIG. 92 is a schematic illustration of an alternative embodiment of a fixed implant supporting flange member. In particular, FIG. 92 shows a fixed implant supporting flange member 9200, which may include openings 9210 through which anchors may be inserted into the implant to secure the implant to tissue of a patient. Openings 9205 may be provided for the cylindrical projections of the rivet strip. Alternatively, this design may be provided with rivet posts of its own, similar to the embodiment shown in FIG. 30.

By using holes 9210 in the fixed flange member, the distal corners of the fixed flange member may be extended to the distal corners of the implant to maximize control of the implant. This design may be used at the distal end of the fixed flange member because the fixed flange member may be curled by hand prior to insertion of the assembly through the cannula. The proximal portion of fixed implant supporting flange member 9200 may remain angled to facilitate egress through the cannula.

Figure 93:
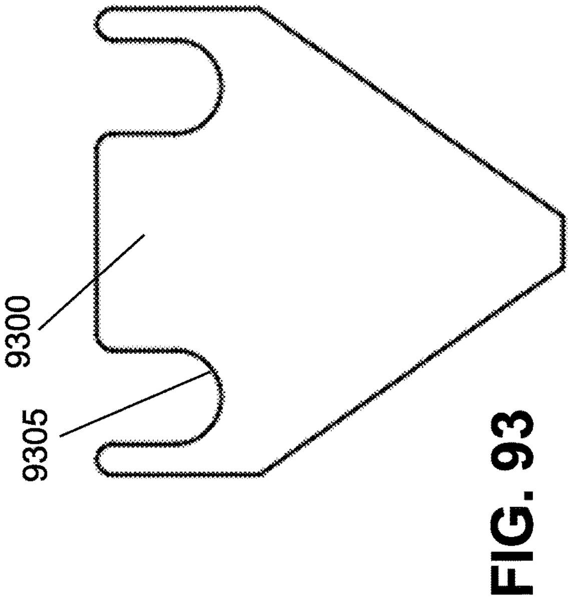
FIG. 93 is a schematic illustration of a movable implant supporting flange member that corresponds with the fixed implant supporting flange member shown in FIG. 92.

FIG. 93 is a schematic illustration of a movable implant supporting flange member 9300 that corresponds with the fixed implant supporting flange member shown in FIG. 92. As shown in FIG. 93, movable flange member 9300 may include slots 9305 at the distal end that correspond with holes 9210 in fixed flange member 9200. Slots 9305 may enable the withdrawal of movable flange member 9300 after anchors have been inserted through the implant.

Figure 94:
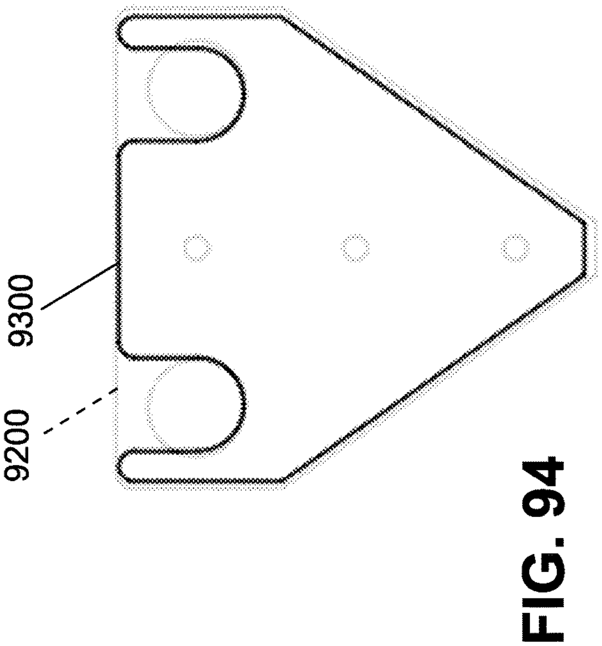
FIG. 94 is a schematic illustration of the size and shape relationship between the fixed implant supporting flange member of FIG. 92 and the movable implant supporting flange member of FIG. 93.

FIG. 94 is a schematic illustration of the size and shape relationship between the fixed implant supporting flange member of FIG. 92 and the movable implant supporting flange member of FIG. 93. Fixed flange member 9200 is shown in phantom for contrast.

It will be noted that both fixed flange member 9200 and movable flange member 9300 may be formed of 0.005" thick UHMWPE.

While various embodiments are described, the description is intended to be exemplary, rather than limiting and it will be apparent to those of ordinary skill in the art that many more embodiments and implementations are possible that are within the scope of the disclosed embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted. Further, unless otherwise specified, any step in a method or function of a system may take place in any relative order in relation to any other step described herein.

What is claimed is:

1. An implant delivery device, comprising:

a handle disposed at a proximal end of the implant delivery device and configured to be grasped by a user;

an outer shaft extending from the handle to a distal end of the implant delivery device; and an implant holding portion proximate the distal end of the implant delivery device, the implant holding portion being configured to releasably retain a sheet-like implant during implantation of the sheet-like implant, wherein the implant holding portion is configured to receive the sheet-like implant between a fixed implant supporting flange member and a movable implant supporting flange member, the fixed implant supporting flange member associated with the outer shaft and configured to support the sheet-like implant on a first side of the sheet-like implant, wherein the fixed implant supporting flange member includes a first substantially triangular-shaped wing and a second substantially triangular-shaped wing that extend from opposing sides of a centerline axis of the outer shaft, wherein the fixed implant supporting flange member is formed with a film material having a thickness, the film material being flexible and resilient such that the first substantially triangular-shaped wing and the second substantially triangular-shaped wing may be at least partially collapsed upon delivery through a cannula, wherein the first substantially triangular-shaped wing includes at least a first window therein, wherein the second substantially triangular-shaped wing includes at least a second window therein, wherein the first window and the second window are both fully surrounded by the film material such that the first window and the second window are separated from one another along the fixed implant supporting flange member by the film material, the first window and the second window configured to: (i) add flexibility to the first substantially triangular-shaped wing and the second substantially triangular-shaped wing, respectively, via an absence of the film material from the first window and the second window; and (ii) expose a first portion and a second portion, respectively, of the sheet-like implant through the fixed implant supporting flange member to allow a first anchor and a second anchor to pass into the sheet-like implant through the first window and the second window, respectively, when the sheet-like implant is being releasably retained by the implant holding portion.

2. The implant delivery device of claim 1, wherein the fixed implant supporting flange member has a maximum width extending from a first tip of the first substantially triangular-shaped wing to a second tip of the second substantially triangular-shaped wing.

3. The implant delivery device of claim 2, wherein the fixed implant supporting flange member further includes a necked-down portion at a distal end thereof, wherein the necked-down portion has a width that is narrower than the maximum width extending from the first tip of the first substantially triangular-shaped wing to the second tip of the second substantially triangular-shaped wing.

4. The implant delivery device of claim 2, wherein at least the first substantially triangular-shaped wing includes a proximal edge that extends at a first angle with respect to the centerline axis and a distal edge that extends at a second angle with respect to the centerline axis, the second angle being larger than the first angle.

5. The implant delivery device of claim 2, wherein the first tip of the first substantially triangular-shaped wing and the second tip of the second substantially triangular-shaped wing are substantially curved.

6. The implant delivery device of claim 2, wherein the first tip of the first substantially triangular-shaped wing and the second tip of the second substantially triangular-shaped wing are substantially elongated, forming elongated edges extending in a longitudinal direction in substantial alignment with the centerline axis.

7. The implant delivery device of claim 1, wherein the film material is a UHMWPE film.

8. The implant delivery device of claim 1, wherein the fixed implant supporting flange member is asymmetrical in the proximal-distal direction.

9. The implant delivery device of claim 1, wherein the first substantially triangular-shaped wing and the second substantially triangular-shaped wing each have one or more edges that are concave.

10. The implant delivery device of claim 1, wherein the thickness of the film material is 0.001 to 0.025 inches.

11. The implant delivery device of claim 1, wherein the movable implant supporting flange member has a surface area that falls completely within a surface area of the fixed implant supporting flange member.

12. The implant delivery device of claim 11, wherein the movable implant supporting flange member has a shape that is substantially similar to a shape of the fixed implant supporting flange member.

13. The implant delivery device of claim 1, wherein the fixed implant supporting flange member includes one or more holes for receiving a rivet of a rivet strip to secure the fixed implant supporting flange member to the outer shaft of the implant delivery device.

14. The implant delivery device of claim 1, wherein the fixed implant supporting flange member includes one or more cylindrical projections forming a rivet configured to secure the fixed implant supporting flange member to the outer shaft of the implant delivery device.

15. The implant delivery device of claim 1, wherein the movable implant supporting flange member is configured to be slidable between a first, distal position and a second, proximal position, wherein, in the first, distal position, the movable implant supporting flange member secures the sheet-like implant against the fixed implant supporting flange member, thus holding the sheet-like implant in an unfurled configuration, and wherein, in the second, proximal position, the movable implant supporting flange member is withdrawn from the distal end of the implant delivery device, thus enabling release of the sheet-like implant.

16. An implant delivery device, comprising:

an implant holding portion proximate a distal end of the implant delivery device, the implant holding portion including a fixed implant supporting flange member and being configured to releasably retain a sheet-like implant during implantation of the sheet-like implant, wherein the fixed implant supporting flange member is associated with an outer shaft of the implant delivery device and includes a first wing and a second wing that extend from a centerline axis of the outer shaft, wherein the fixed implant supporting flange member is formed with a film material having a thickness, the film material being flexible and resilient such that the first wing and the second wing may be at least partially collapsed upon delivery through a cannula, wherein the first wing includes at least a first window therein, wherein the second wing includes at least a second window therein, wherein the first window and the second window are both fully surrounded by the film material such that the first window and the second window are separated from one another along the fixed implant supporting flange member by the film material, the first window and the second window configured to: (i) add flexibility to the first wing and the second wing, respectively, via an absence of the film material from the first window and the second window; and (ii) expose a first portion and a second portion, respectively, of the sheet-like implant through the fixed implant supporting flange member to allow a first anchor and a second anchor to pass into the sheet-like implant through the first window and the second window, respectively, when the sheet-like implant is being releasably retained by the implant holding portion.

17. The implant delivery device of claim 16, further including a movable implant supporting flange member, the implant holding portion being configured to receive the sheet-like implant between the movable implant supporting flange member and the fixed implant supporting flange member.

18. The implant delivery device of claim 17, wherein the sheet-like implant is releasably retained in a recess by the movable implant supporting flange member and the fixed implant supporting flange member.

19. The implant delivery device of claim 18, wherein the movable implant supporting flange member is configured to be movable between a first position in which the movable implant supporting flange member holds the sheet-like implant within the recess and a second position in which the sheet-like implant is unencumbered by the movable implant supporting flange member, thus enabling release of the sheet-like implant from the implant holding portion of the implant delivery device.

20. The implant delivery device of claim 19, wherein the first window and the second window are located in opposite distal corners of the fixed implant supporting flange member, and wherein the movable implant supporting flange member includes corresponding first and second slots therein that at least partially overlap the first window and the second window, respectively, when the movable implant supporting flange member is in the first position so as to allow the first anchor and the second anchor to pass through the first slot and the second slot, respectively, when the movable implant supporting flange member is in the first position.

* * * * *